(12) United States Patent  (10) Patent No.: US 7,588,438 B2
Xu et al.  (45) Date of Patent: Sep. 15, 2009

(54) SYSTEM, METHOD AND APPARATUS FOR FIBER SAMPLE PREPARATION FOR IMAGE ANALYSIS

(75) Inventors: Bugao Xu, Austin, TX (US); Wurong Yu, Zhejiang (CN)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/590,067

(22) Filed: Oct. 31, 2006

(65) Prior Publication Data

US 2007/0103668 A1   May 10, 2007

Related U.S. Application Data

(60) Provisional application No. 60/732,303, filed on Nov. 1, 2005.

(51) Int. Cl.
*B26D 1/00* (2006.01)
*B26D 7/00* (2006.01)

(52) U.S. Cl. .............................. 425/313; 83/24; 83/167; 83/618; 83/913

(58) Field of Classification Search .................. 425/73, 425/77, 82.1, 142, 196, 295, 307, 309, 313, 425/316; 83/23–24, 98, 100, 167, 618, 694, 83/620, 913, 919, 78, 99, 165
See application file for complete search history.

(56) References Cited

U.S. PATENT DOCUMENTS

| | | | | |
|---|---|---|---|---|
| 1,016,439 A | * | 2/1912 | Peters .......................... | 83/167 |
| 2,143,123 A | * | 1/1939 | Erickson ....................... | 83/168 |
| 3,035,470 A | * | 5/1962 | Tolerico ....................... | 83/168 |
| 3,280,681 A | * | 10/1966 | Turner .......................... | 83/169 |
| 3,334,532 A | * | 8/1967 | Mylo ............................ | 83/18 |
| 3,334,533 A | * | 8/1967 | Davis, Jr. ..................... | 83/100 |
| 3,776,084 A | * | 12/1973 | Slyvakov ...................... | 83/342 |
| 3,915,042 A | * | 10/1975 | Laird ........................... | 83/341 |
| 3,941,530 A | * | 3/1976 | Platt ........................... | 425/83.1 |
| 4,228,709 A | * | 10/1980 | Guzay et al. .................. | 83/620 |
| 4,285,258 A | * | 8/1981 | Logan et al. .................. | 83/410 |
| 4,445,408 A | * | 5/1984 | Keith ............................ | 83/37 |
| 4,600,462 A | * | 7/1986 | Watt ............................ | 156/278 |
| 5,106,006 A | * | 4/1992 | Suda et al. .................... | 225/2 |
| 5,163,348 A | * | 11/1992 | Kitada et al. .................. | 83/13 |
| 5,249,492 A | * | 10/1993 | Brown et al. .................. | 83/23 |
| 5,513,805 A | * | 5/1996 | Fisher et al. ................. | 241/18 |

(Continued)

FOREIGN PATENT DOCUMENTS

EP   202676 A2 * 11/1986

*Primary Examiner*—Philip C Tucker
*Assistant Examiner*—Dimple N Bodawala
(74) *Attorney, Agent, or Firm*—Chainey P. Singleton; Edwin S. Flores; Chalker Flores, LLP

(57) ABSTRACT

The present invention is an apparatus, system and method for preparing samples for analysis including a mechanical fiber cutting apparatus. The mechanical fiber cutting apparatus has two or more cutter blades under the control of a blade moving mechanism. A fiber chamber is positioned to receive the one or more cut fibers created by the cutting action of the two or more cutter blades. The pressurized gas source connected to the fiber chamber transfers the one or more cut fibers into a sample preparation housing. The one or more cut fibers are distributed randomly onto a sample slide within the sample preparation housing.

6 Claims, 23 Drawing Sheets

U.S. PATENT DOCUMENTS

| | | | | |
|---|---|---|---|---|
| 5,647,265 A * | 7/1997 | Johnson et al. | | 83/861 |
| 5,658,601 A * | 8/1997 | Hoshi | | 425/289 |
| 5,704,266 A * | 1/1998 | Takehara | | 83/114 |
| 5,894,773 A * | 4/1999 | Sevenish et al. | | 83/13 |
| 6,142,045 A * | 11/2000 | Coxe | | 83/23 |
| 6,334,378 B1 * | 1/2002 | Tsuzaki et al. | | 83/39 |
| 6,604,929 B2 * | 8/2003 | Hawley et al. | | 425/313 |
| 6,663,372 B2 * | 12/2003 | Ready et al. | | 425/67 |
| 6,799,496 B2 * | 10/2004 | Verhaeghe | | 83/167 |
| 7,004,413 B2 * | 2/2006 | Langlois | | 241/242 |
| 2004/0011171 A1 * | 1/2004 | Hamilton | | 83/24 |
| 2004/0195719 A1 * | 10/2004 | Ishii et al. | | 264/177.12 |
| 2005/0042323 A1 * | 2/2005 | Habisreitinger et al. | | 425/472 |
| 2005/0120843 A1 * | 6/2005 | Allwein et al. | | 83/19 |
| 2006/0006572 A1 * | 1/2006 | Kindle et al. | | 264/69 |

\* cited by examiner

| Code: | 1 | 5 | 49 | 165 | 255 |

FIG. 11

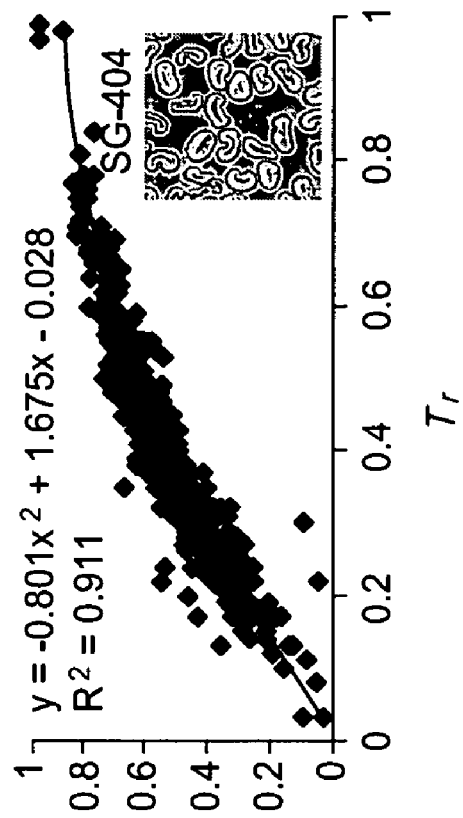
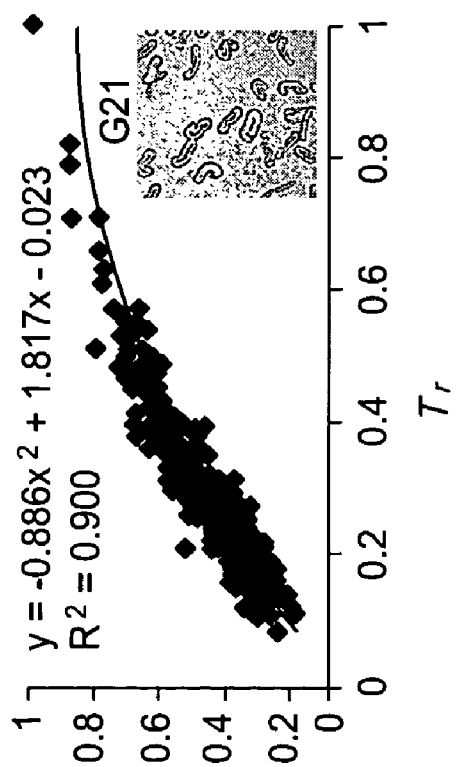
FIG. 25B
FIG. 25A

SYSTEM, METHOD AND APPARATUS FOR FIBER SAMPLE PREPARATION FOR IMAGE ANALYSIS

CROSS-REFERENCE TO RELATED APPLICATIONS

This application claims priority to U.S. Provisional Application Ser. No. 60/732,303, filed Nov. 1, 2005, the contents of which are incorporated by reference herein in its entirety.

This invention was made with U.S. Government support under United States Department of Agriculture grant No. is 2003-35504-12855.

TECHNICAL FIELD OF THE INVENTION

The present invention relates in general to the field of sample preparation, and more particularly, to fiber sample preparation for analysis of physical characteristics.

BACKGROUND OF THE INVENTION

Without limiting the scope of the invention, its background is described in connection with fiber sample preparation devices for analysis, as an example. Natural fibers (e.g., cotton) are commonly used as textile materials with fiber quality remain one of the most serious issues for the world's textile industry. There is a perception among textile manufacturers that some cotton is of lesser quality than other cottons; however, these perceptions of quality are generally not expressed quantitatively.

Generally, natural fibers are divided into grades that are dependent on fiber maturity, fineness, contamination (e.g., from a variety of sources surrounding vegetation, and insects) and damage (e.g., from cotton harvesting and handling). The growth and storage conditions of the natural fibers also play a role in the condition and maturity of the cotton fiber. The grade of the fiber will ultimately determine the use of the fiber in materials and garments.

One factor that influences the grade of the fiber, determines its use in production, spinning and ginning processes and therefore directly affects the value of the cotton in the market place is the maturity of the fiber. For example, the presence of immature cotton fibers poses significant problems in processing performance and in the quality of the finished textile, e.g., the neps, weak places in yarns, ends-down in spinning, excess waste, dyeing imperfections, white specks and barré. The maturity of the fiber can be determined through analysis of the physical characteristics of the fiber.

Generally, a cotton fiber is an elongation of a single epidermal cell on the surface of the seed and the maturity of that fiber refers to the degree of thickening of the fiber cell wall relative to the perimeter or effective diameter of the fiber. The degree of development of the fiber wall is one indication of fiber maturity. Other physical characteristics indicative of the quality of the fiber are the cross sectional profile and the length of the fiber. The cross sectional profile or morphology of the fiber is determined by the cell wall area and the perimeter of the fiber cross-section; however, the circularity or degree of thickening is also important in determining the quality of the fiber.

One method used extensively in the textile field for grading fibers is batch testing, which is a compilation of measurements from many different instruments. One indicator used by cotton growers to determine fiber quality is the length and the cross-sectional profile of the fiber. However, the current batch testing techniques are not practical for use in commercial operations due in-part to their slow process speed. Currently, High Volume Instrument (HVI) and Advanced Fiber Information System (AFIS) are used to characterize the fibers by measuring physical and mechanical properties (e.g., length and shape) of fiber (e.g., cotton) at rates upwards of 1000 per second. AFIS is an aeromechanical separator with a single entity sensor and computer for data collection and analysis. The AFIS separates fibers and neps into one air stream, and trash into another air stream. The fibers and neps are then monitored using optical-based sensors and analyzed.

One disadvantage of devices currently in use include the lack of accuracy and precision of fiber length measurement, due in part to the tendency of the device to measure two partially overlapping fibers as one and the inability of the device to distinguish whether a fiber is doubled over upon itself or straight. Current methods must sample tens of thousands of times to obtain reproducible data; however, accuracy is still limited.

Another disadvantage of devices currently in use includes the lack of accuracy and precision because of inconsistencies in the preparation of samples for analysis. Current samples preparation techniques used in the art produces non-uniformed cuts at the ends of the fiber segments (e.g., angle variations from the perpendicular) and have a tendency to produce samples with partially overlapping fibers.

SUMMARY OF THE INVENTION

The foregoing problems have been recognized for many years and while numerous solutions have been proposed, none of them adequately address all of the problems in a single device, e.g., accuracy and precision sample preparation producing randomly dispersed fibers.

The present inventor recognized a need for an apparatus, method and system for preparing fiber sample to be imaged in an automated manner to increased accuracy, precision and reproducibility of the sample, while reducing errors in fiber widths and distortions in width measurements due to crossed, touching or overlapping fibers.

For example, the present invention includes a mechanical fiber cutting apparatus. The mechanical fiber cutting apparatus has two or more cutter blades under the control of a blade moving mechanism. The cutting action of the two or more cutter blades creates one or more cut fibers. A fiber chamber is positioned to receive the one or more cut fibers and a pressurized gas source connected to the fiber chamber. The pressurized gas source releases the gas to transfers the one or more cut fibers into a sample preparation housing. As the gas travels through the fiber chamber, the one or more cut fibers are carried along to the sample preparation housing. Upon entering the sample preparation housing the fibers are dispersed and allowed a random distribution of the fibers on the sample slide within the sample preparation housing.

The present invention includes a pneumatic fiber cutting apparatus having two or more cutter blades under the control of a blade moving mechanism. The cutting action of the two or more cutter blades creates one or more cut fibers. The pneumatic fiber cutting apparatus includes a fiber chamber positioned to receive the one or more cut fibers. The fiber chamber has a pressure inlet connected to a pressurized gas source, an outlet tube connected to a sample preparation housing and two or more slots that accept the two or more cutter blades. One or more sample slides are positioned within the sample preparation housing. Upon operation, a sample of one or more fibers is cut with the two or more cutter blades to create one or more cut fibers, which fall into the fiber chamber. The two or more cutter blades enter the two or more slots to at least partially seal the fiber chamber. The pressurized gas source releases a gas into the pressure inlet of the fiber chamber to transport the one or more cut fibers to the sample preparation housing. Upon entering the sample preparation housing the fibers are dispersed randomly onto the one or more sample slides.

The present invention also includes a method of preparing a fiber sample for analysis by positioning a fiber sample onto a mechanical fiber cutting apparatus that includes two or more cutter blades under the control of a blade moving mechanism and a fiber chamber. The fiber chamber includes a housing in communication with a pressurized gas and in communication with a sample preparation housing. The cutting action of the two or more cutter blades create one or more cut fibers and deposits the one or more cut fibers into the fiber chamber. One or more pulses from the pressurized gas source are released to transport the one or more cut fibers to the sample preparation housing as the one or more cut fibers enter the sample preparation housing with the gas. The one or more cut fibers are distributed randomly onto a sample slide within the sample preparation housing.

The present invention also includes image-processing algorithms for analyzing longitudinal images of fibers (e.g., cotton) in an automatic system, having improved accuracy and/or efficiency. The adaptive thresholding algorithm of the present invention reduces the errors arising from unfocused fibers and the look-up table increases the efficiency of tracing fiber edges. The double-scanning algorithm enhances the accuracy of the transverse scans of fibers, while the validation rules prevent false scans from being included in the output. A merging algorithm links short fiber segments that belong to the same fiber to evaluate the fiber twists.

One embodiment of the present invention provides a system having an image analysis algorithm developed for a microscopic system that specifically evaluates cotton properties from longitudinal views. The system utilizes a motorized stage to transport a sample slide to grab sequential images of fiber segments, scans transversely the detected fibers in the images, and outputs both fineness and maturity measurements of cotton, based on the statistic data of the massive scans across fibers.

The present invention also includes a method of monitoring the fineness and maturity of fibers by acquiring one or more images of the fibers and processing the image to identify characteristics of the fibers. The processing includes determining the intensity of one or more regions of the images and comparing the intensity of one of the regions to the intensity of another region to designate the fineness and maturity of the fibers.

The processing step further includes removing one or more boundary pixels from the images of the fibers. The one or more boundary pixels have three or fewer black neighboring pixels and re-scanning the images for the one or more boundary pixels until no black pixel exists in the image. The method further includes identifying one or more holes that fall on the one or more fibers to produce a lumen image and omitting the one or more holes that do not passed through the one or more fibers. The images of the fibers and the lumen images are merged and the pixels in the images of the fibers and the pixels in the lumen image are compared, wherein identical pixels are set to black.

The present invention also provides a system for determining the maturity of one or more fibers including a digital imaging device positioned to capture one or more images of one or more fibers and an image processing device that processes the one or more images to identify one or more fiber characteristics. The imaging processing device determines the intensity of one or more regions of the one or more images and compares the intensity of one of the one or more regions to the intensity of another of the one or more regions. The regions are then graded and designated as to the maturity and grade of the fiber.

A fiber maturity measurement apparatus is provided for determining the maturity of one or more fibers conditions having a digital imaging device positioned to capture one or more images of one or more fibers and an image processing device that processes the one or more images to identify fiber characteristics. The imaging processing device determines the intensity of one or more regions of the one or more images and compares the intensity of one of the one or more regions to the intensity of another of the one or more regions.

BRIEF DESCRIPTION OF THE DRAWINGS

For a more complete understanding of the features and advantages of the present invention, reference is now made to the detailed description of the invention along with the accompanying figures and in which:

FIG. 11 is a table of possible values for edge tracing in the up-right direction;

FIG. 14A is prior to validation and FIG. 14B is post validation;

FIG. 16A is a plot of the longitudinal data using cross-sectional data, while

FIG. 22A is an image of the cross section of the fibers in lumens, while FIG. 22B is an image of the measurable cross sections;

FIG. 25 is a plot of the circularity and the degree of thickening of different fibers;

DETAILED DESCRIPTION OF THE INVENTION

Figure 1:
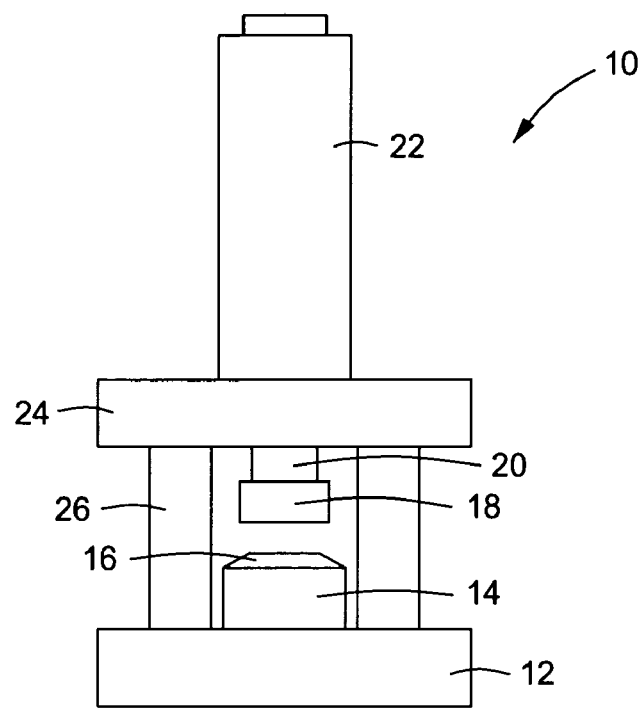
FIG. 1 illustrates certain features of a cutting apparatus according to an embodiment of the present invention.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

In accordance with the present invention, a method and apparatus are provided that allows precise cutting, trimming or separating of materials using a multi-blade cutting tool. The present invention provides a cutting apparatus for cutting, trimming and separating materials into defined lengths and producing randomized distributions of the materials to facilitate imaging and analysis of the materials without undue manipulation.

For example, the present invention includes a mechanical fiber cutting apparatus. The mechanical fiber cutting apparatus has two or more cutter blades under the control of a blade moving mechanism. The cutting action of the two or more cutter blades creates one or more cut fibers. A fiber chamber is positioned to receive the one or more cut fibers. A pressurized gas source is connected to the fiber chamber to release the gas and transfers the one or more cut fibers into a sample preparation housing. As the gas travels through the fiber chamber, the one or more cut fibers are carried along to the sample preparation housing. Upon entering the sample preparation housing the fibers are dispersed and allowed to deposit onto a sample slide. The one or more cut fibers are distributed randomly onto the sample slide within the sample preparation housing.

A series of two or more cutter blades can be used to cut a fiber into multiple segments of similar lengths (e.g., equidistant spaced blades) or different lengths (e.g., non-equidistant spaced blades). Alternatively, the series of blades may be used to cut a bundle of fibers into multiple segments of similar lengths (e.g., equidistant spaced blades) or different lengths (e.g., non-equidistant spaced blades).

The two or more cutter blades include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more blades. The two or more cutter blades are substantially parallel; however, the blades may be angled (e.g., from about 0 to about 180 degrees) and/or tilted (e.g., from about 10 to about 170 degrees) in some embodiments. The angles and/or tilts may be the same for each of the two or more cutter blades, the angle may be the same and the tilt varied, the tilt may be the same and the angle varied, both the angle and the tilt may be varied or any combination thereof that may be needed for a particular application. The two or more cutter blades may be individually a conventional razor blade, a blade, a serrated blade, a metal wire, a plastic fiber, a composite fiber, a plastic blade, or a composite material or mixtures thereof.

The fiber chamber includes a connection for the pressurized gas source and a connection to the sample preparation housing to allow the one or more cut fibers to be transferred. The sample preparation housing and the fiber chamber may be connected through a tube. The tube may have a profile that is round, polygonal, square, oval, rectangular, triangular, or any other shape desired. In addition, the tube may be made from a variety of materials including plastics, composites, polymers, metals, and similar materials.

The pressurized gas source may include a compressor, a tank, a gas line, or a combination thereof and may be connected directly to the fiber chamber or via a manifold system. In addition, the pressurized gas may be used to power the blade moving mechanism when in the form of a pneumatic or hydraulic ram. The pressurized gas source includes pressurized air, nitrogen, hydrogen, oxygen, carbon dioxide, carbon monoxide, or a mixture thereof.

The skilled artisan will recognize that the present invention may also use a vacuum system to move the one or more cut fibers from the fiber chamber to the sample preparation housing. For example, a vacuum may be applied to the system at the sample preparation housing causing the one or more cut fibers to be transported from the fiber chamber to the sample preparation housing. Once the one or more fibers are within the sample preparation housing, the vacuum may be discontinued allowing the one or more cut fibers to fall to a random distribution on the sample slide within the sample preparation housing.

The present invention also includes a pneumatic fiber cutting apparatus having two or more cutter blades under the control of a blade moving mechanism. The cutting action of the two or more cutter blades creates one or more cut fibers. The pneumatic fiber cutting apparatus includes a fiber chamber positioned to receive the one or more cut fibers. The fiber chamber has a pressure inlet connected to a pressurized gas source, an outlet tube connected to a sample preparation housing and two or more slots that accept the two or more cutter blades. One or more sample slides are positioned within the sample preparation housing. Upon operation, a sample of one or more fibers is cut with the two or more cutter blades to create one or more cut fibers, which fall into the fiber chamber. The two or more cutter blades enter the two or more slots to at least partially seal the fiber chamber. The pressurized gas source releases a gas into the pressure inlet of the fiber chamber to transport the one or more cut fibers to the sample preparation housing. Upon entering the sample preparation housing the fibers are dispersed and allowed to deposit onto a sample slide. The one or more cut fibers are distributed randomly onto the one or more sample slides. A cover slide may be placed over the one or more sample slides to allow removal, while retaining the random sample distribution.

The present invention also includes a system for preparing a sample of one or more fibers. The system includes two or more cutter blades under the control of a blade moving mechanism. The cutting action of the two or more cutter blades creates one or more cut fibers. The system also includes a fiber chamber positioned to receive the one or more cut fibers and a pressurized gas source connected to the fiber chamber that transfers the one or more cut fibers into a sample preparation housing. The one or more cut fibers are thereby distributed randomly onto a sample slide. The system also includes an imaging system for imaging the one or more cut fibers distributed randomly onto a sample slide.

The present invention also provides an imaging system that has a digital imaging device and an image processing device. The digital imaging device is positioned to capture one or more images of one or more fibers. The image processing device determines the intensity of one or more regions of the one or more images and compares the intensity of one of the one or more regions to the intensity of another of the one or more regions. The image processing device can then determine if the region is defective and should be labeled as such.

The present invention includes a method of preparing a fiber sample for analysis by positioning a fiber sample onto a mechanical fiber cutting apparatus. The mechanical fiber cutting apparatus includes two or more cutter blades under the control of a blade moving mechanism, a fiber chamber having a pressurized gas source in communication with the fiber chamber and a sample preparation housing in communication with the fiber chamber. The cutting action of the two or more cutter blades create one or more cut fibers and deposits the one or more cut fibers into the fiber chamber. One or more pulses from the pressurized gas source are released to transport the one or more cut fibers to the sample preparation housing. The one or more cut fibers are distributed randomly onto the sample preparation housing and allowed to form a random distribution on a sample slide within the sample preparation housing.

With reference to FIG. 1, a cutting apparatus 10, in accordance with the present invention is shown and includes a base plate 12 having a fiber chamber 14 attached thereto. The fiber chamber 14 has a blade receiving plate 16 to receive two or more cutting blades 18. The two or more cutting blades 18 are attached to a movable piston 20, which is attached to a piston moving mechanism 22. The piston moving mechanism 22 is in communication with a top mounting plate 24 and supported by a support mechanism 26 attached to the base plate 12.

The piston moving mechanism 22 may be any moving mechanism that produces movement of the piston 20. The piston moving mechanism 22 may be a hydraulic mechanism (e.g., a ram or a press) that uses a fluid to move the piston 20 or a pneumatic mechanism (e.g., a ram or a press). The hydraulic system transfers force applied at one point to another point using an incompressible fluid. Both the hydraulic system and the pneumatic mechanism allow the addition of force multiplication (or division) to the system by a change in the size of the piston and/or cylinder. In addition, the piston moving mechanism 22 may be a motor (e.g., gas, diesel, electric, hybrid motor, water, solar, human and combinations thereof), which is used in conjunction with gears to move the piston 20. Furthermore, combinations of mechanisms may be used to move the piston 20. For example, an electric motor (not shown) may be used to create pneumatic pressure in a system (not shown) that in turn moves the piston 20. Additionally, the movable piston 20 may be moved manually. The skilled artisan recognizes the many different types of systems that may be used for this purpose.

Figure 2:
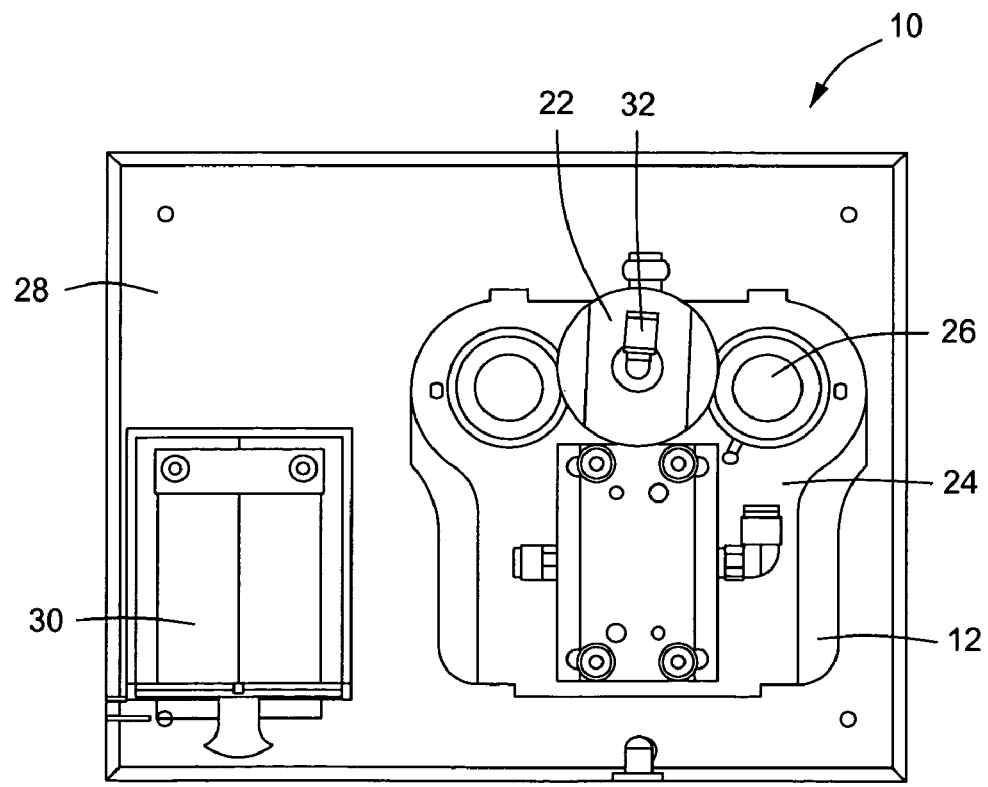
FIG. 2 is a top view of a portion of the apparatus shown in FIG. 1.

With reference to FIG. 2, a top view of the cutting apparatus 10, in accordance with the present invention is shown and includes a sample platform 28, which supports a sample preparation chamber 30 and a base plate 12. The base plate 12 has a fiber chamber (not shown) attached thereto with a blade receiving plate (not shown) to receive the cutting blades (not shown). The cutting blades (not shown) are attached to a movable piston (not shown) operated by a piston moving mechanism 22. The piston moving mechanism 22 has a pressure fitting 32 attached to control the movement of the piston (not shown). The piston moving mechanism 22 is in contact with a top mounting plate 24 and is supported by a support mechanism 26 attached to the base plate 12. A sample preparation chamber 30 is located on the sample platform 28 in such a manner that communication may be established with the fiber chamber 14. The communication may be in the form of a tube (not shown) connecting the fiber chamber 14 and the sample preparation chamber 30. However, the skilled artisan will recognize there are many ways to communicate between containers, e.g., mechanical mechanisms (e.g., belts), pneumatic (e.g., air blasts), electrostatic interaction, gravity and the like.

Figure 3:
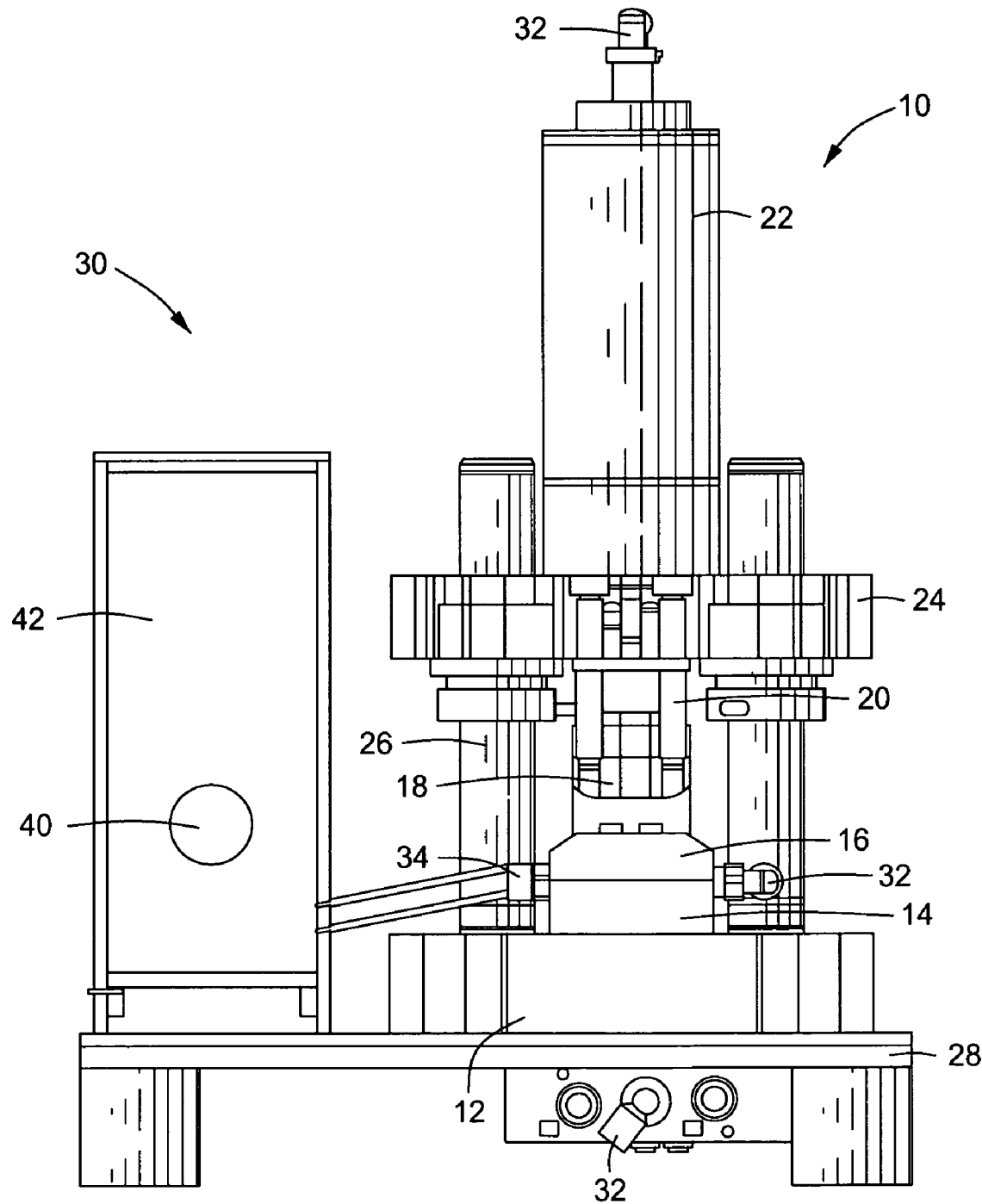
FIG. 3 is a front view of a portion of the apparatus shown in FIG. 1.

With reference to FIG. 3, a front view of one embodiment of the cutting apparatus 10, in accordance with the present invention is shown and includes a sample platform 28, which supports a sample preparation chamber 30 and a base plate 12. The base plate 12 includes a fiber chamber 14 attached thereto. A pressure fitting 32 is fitted to the fiber chamber 14 to allow the induction of a force into the inside of the fiber chamber 14. An outlet tube fitting 34 is also fitted to the fiber chamber 14 to connect a fiber tube (not shown) to the sample preparation chamber 30, thus, allowing conduction of materials within the fiber chamber 14 to the sample preparation chamber 30. The fiber chamber 14 has a blade receiving plate 16 to receive the two or more cutting blades 18. The two or more cutting blades 18 are attached to a movable piston 20, which is attached to a piston moving mechanism 22. The piston moving mechanism 22 is connected to a top mounting plate 24 and is supported by a support mechanism 26 attached to the base plate 12. In addition, the cutting apparatus 10 may include one or more switches (not shown) responsible for activating the piston moving mechanism 22 or the supply of gas, electric, fluid or combination thereof used in devices, e.g., hydraulic or pneumatic. A regulator (not shown) may also be used to control the pressure and other factors as needed. The regulator (not shown) may be attached to the sample platform 28 directly or adjacently to communicate with the desired components.

The sample preparation chamber 30 is attached (e.g., screws, bolts, pegs, loop and hook fasteners, glue, tape, epoxy, welds, fused, soldered bolts, pegs and the like) to the sample platform 28; however, the sample preparation chamber 30 may be attached by gravity. The sample preparation chamber 30 is generally a closed container and includes a door handle 40 attached to a door 42 to allow access to the sample preparation chamber 30. The sample preparation chamber 30 may have one or more walls depending on the shape of the container, e.g., spherical, cubical, pyramidal, etc. Furthermore, the interior space of the sample preparation chamber 30 may have internal baffles or walls to direct the flow (not shown). The sample preparation chamber 30 may be made of any material desired by the artisan, e.g., glass, metal, alloy, wood, stone, plastic, fiber, polymer, composite, fiberglass and combinations thereof.

In operation, the fibers (not shown) are cut by the cutting apparatus 10. Upon activation, the piston moving mechanism 22 moves the piston 20 and the two or more cutting blades 18 through the fibers (not shown) to generate cut fibers (not shown). The cut fibers (not shown) fall into the fiber chamber 14 through the blade receiving plate 16. The blade receiving plate 16 is designed to accommodate the movement of the two or more cutting blades 18 and seal the fiber chamber 14 as the two or more cutting blades 18 penetrate the fiber chamber 14. A force is applied through the pressure fitting 32 and into the fiber chamber 14. The cut fibers (not shown) in the fiber chamber 14 are dislodged and travel to the outlet tube fitting 34 to the sample preparation chamber 30. The cut fibers (not shown) obtain a random distribution as they are dispersed through the outlet tube fitting 34 into the space of the sample preparation chamber 30. One or more sample holders (not shown) may be placed in the sample preparation chamber 30 to allow the cut fibers to have a randomized distribution. The one or more sample holders (not shown) may be a slide, a disc, a plate, a tray or other surface known to the skilled artisan. In some instances, the one or more sample holders (not shown) are covered by a top slide, a cover slide or a cover upon movement from the sample preparation chamber 30 for processing.

Figure 4:
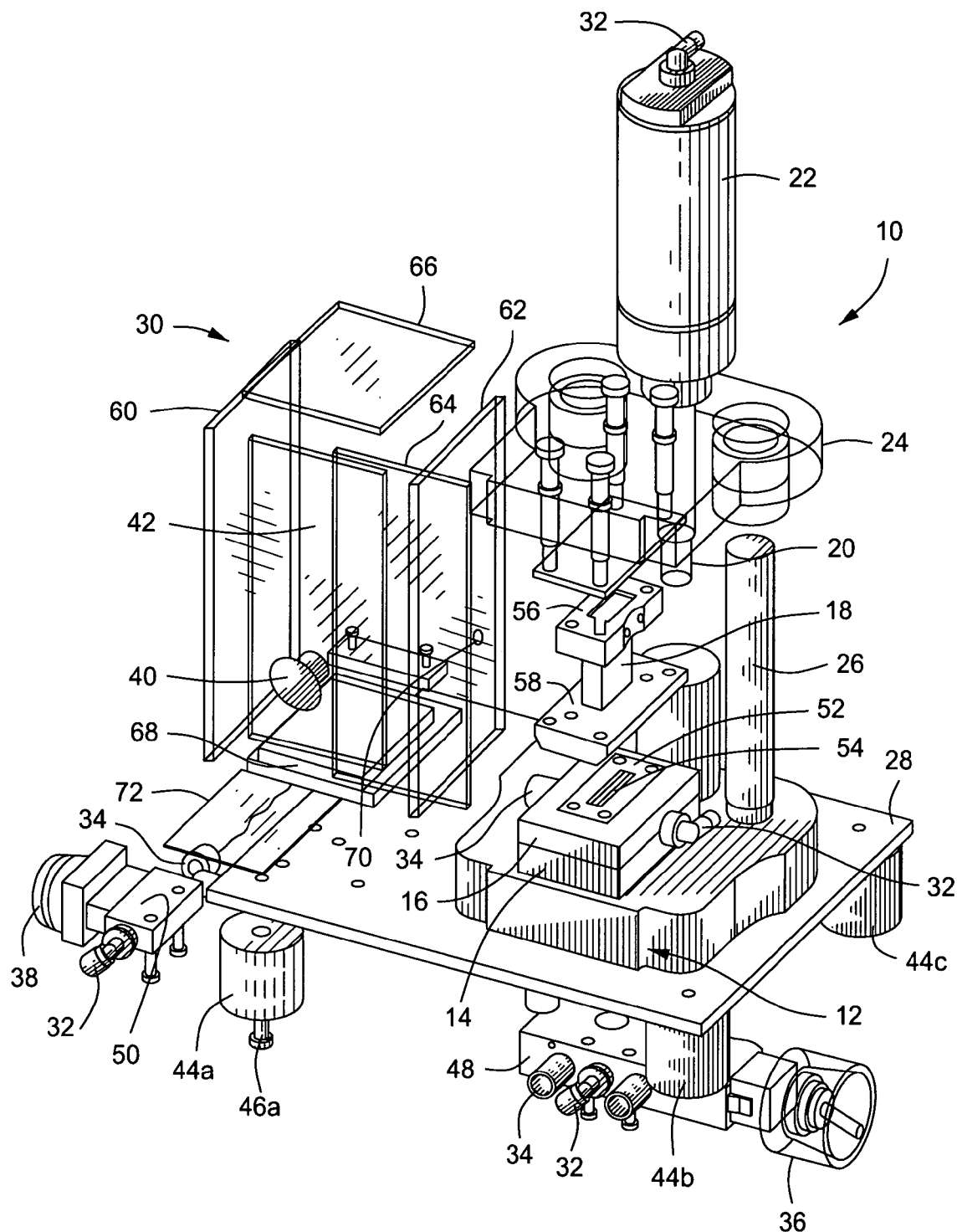
FIG. 4 is a partially exploded perspective view of a portion of the apparatus shown in FIG. 1.

With reference to FIG. 4, a partially exploded perspective view of one embodiment of the cutting apparatus 10, in accordance with the present invention is shown and includes a sample platform 28, which supports a sample preparation chamber 30 and a base plate 12. The sample platform 28 will differ depending on the particular needs of the specific embodiment being used. The sample platform 28 may serve as a mounting surface for the attachment of various components. The sample platform 28 may include stabilization legs 44a, 44b, 44c and 44d (not shown), which may have adjusters 46a to adjust the height of the sample platform 28 and/or to level the cutting apparatus 10. In addition, the sample platform 28 may include one or more switches 36 attached to a distribution block 48 that distributes current, air, electricity, fluid, gas, liquid and other materials used in or by the cutting apparatus 10. The distribution block 48 may also include one or more pressure fittings 32; outlet tube fittings 34; electrical connections devices (not shown), gas connections devices (not shown) and combinations thereof. A second regulator block 50 may also be connected to the sample platform 28. The second regulator block 50 may also include one or more pressure fittings 32; outlet tube fittings 34; electrical connections devices (not shown), gas connections devices (not shown) and combinations thereof. A regulator 38 may be connected to the sample platform 28, the distribution block 48, the second regulator block 50 or a combination thereof. Alternately, the components may be connected to the base plate 12 directly.

The base plate 12 contacts the sample platform 28 and serves as the base of the cutting apparatus 10. A fiber chamber 14 is attached to the base plate 12 and a blade receiving plate 16. A pressure fitting 32 is fitted to the fiber chamber 14 to allow a flow inside the fiber chamber 14. An outlet tube fitting 34 is also fitted to the fiber chamber 14 to connect a fiber tube (not shown) to the sample preparation chamber 30, thus, allowing transfer of materials within the fiber chamber 14 to the sample preparation chamber 30.

The fiber chamber 14 has a blade receiving plate 16 to receive the two or more cutting blades 18. A blade slot plate 52 is provided that accepts the two or more cutting blades 18 and is attached to the fiber chamber 14. The blade slot plate 52 has two or more blade slots 54, which allow the two or more cutting blades 18 to pass through the sample (not shown) and into the blade receiving plate 16. The clearance between the two or more blade slots 54 and the two or more cutting blades 18 may be varied to accommodate different materials. The number of cutting blades 18 will depend on the preference of the user and the physical constraints of the cutting apparatus 10. For example one cutting apparatus 10 includes 2, 3, 4, 5, 6, 7, 8, 9, 10, 11, 12, 13, 14, 15, 16, 17, 18, 19, 20 21, 22, 23, 24, 25, 26, 27, 28, 29, 30 or even more than 30 cutting blades 18. Furthermore, the spacing between the two or more cutting blades 18 may be varied depending on the application. The two or more cutting blades 18 cut the sample as they pass through the sample. The separation between one blade and the next blade determines the length of the fiber. Therefore, by changing the spacing separating the two or more cutting blades 18 the size of the cut fiber will be changed. For example, the spacing between the individual blades may be kept constant to create uniformed fibers; however, in some instances a variety of distances may be necessary to provide a distribution of differently sized for the samples. Alternatively, the individual cutting blades 18 may be spaced in a pattern of distinct distances.

The two or more cutting blades 18 are generally perpendicular to the fiber chamber 14 and parallel to each other blade. In addition, the angle that the two or more cutting blades 18 cut the sample may be configured to produce different angles as necessary. The angle can be any angle desired by adjusting the vertical angle to create a bevel or the horizontal angle to create an angled cut. A compound angle may also be produced by varying the vertical and horizontal angles at the same time. These type cuts and angles (e.g., angle, bevel, miter etc.) are well within the knowledge of the skilled artisan. Alternatively, the two or more cutting blades 18 can independently be positioned to form a right or left angle of between about one and ninety degrees relative to the individual cutting blades 18. The two or more cutting blades 18 can include individually, either entirely or in part, a conventional razor blade, a blade, a serrated blade, a metal wire, a plastic fiber, a composite fiber, a plastic blade, a composite material or some other device having an surface that can be used for cutting.

The two or more cutting blades 18 may be attached to a cutting blade holder 56 that secures the two or more cutting blades 18 and fixes the position, angle and spacing of the individual blades. The cutting blade holder 56 may be in the form of an individual blade replaceable holder or a cartridge replacement wherein the entire cutting blade holder 56 is replaced as a unit. The cutting blade holder 56 may also include a middle plate 58 attached to the two or more cutting blades 18 for the attachment to the top mounting plate 24, seal the fiber chamber 14 or combinations thereof. The middle plate 58 may be made of a metal, an alloy, a plastic, a polymer, a composite, foam, latex, rubber, or a combination thereof.

The two or more cutting blades 18 are attached to a movable piston 20, which is attached to a piston moving mechanism 22. The two or more cutting blades 18 may be attached directly to the piston 20 or through an intermediate structure such as the top mounting plate 24. Alternatively, the two or more cutting blades 18 may be attached to the middle plate 58, which is attached to the top mounting plate 24 or the piston 20. The skilled artisan will recognize the numerous mounting options to mount the two or more cutting blades 18 to the piston 20.

The piston moving mechanism 22 is connected to a top mounting plate 24 and is supported by a support mechanism 26 attached to the base plate 12. The piston moving mechanism 22 may be a piston 20 that is activated by increasing the pressure within the piston moving mechanism 22 to extend the piston 20, which in turn cause the two or more cutting blades 18 to move. The piston moving mechanism 22 may include one or more pressure fitting 32 to allow pressure to be applied, e.g., increased, decreased or maintained.

The sample preparation chamber 30 is attached (e.g., screws, bolts, pegs, loop and hook, glue, tape, epoxy, welds, fused, soldered, bolts, pegs and the like) to the sample platform 28; however, the sample preparation chamber 30 may be attached by gravity or friction fitting. The sample preparation chamber 30 is generally a closed container. For example, the sample preparation chamber 30 is made of opposing side walls 60 and 62 connected by a back wall 64, a top wall 66 and a bottom wall 68. Access to the sample preparation chamber 30 is through the door 42 using the door handle 40. The side wall 62 contains a sample preparation chamber aperture 70 that allows the conduction of samples from the fiber chamber 14 to the sample preparation chamber 30. A sample collection device 72 is placed in the sample preparation chamber 30 whereby the cut fibers may form a random distribution on the sample collection device 72.

The sample preparation chamber 30 included a door handle 40 attached to a door 42 to allow access to the sample preparation chamber 30. The sample preparation chamber 30 may have one or more walls depending on the shape of the container, e.g., spherical, cubical, pyramidal, etc. Furthermore, the interior space of the sample preparation chamber 30 may have internal baffles or walls to direct the flow (not shown). The sample preparation chamber 30 may be made of any material desired by the artisan will suffice, e.g., glass, metal, alloy, wood, stone, plastic, fiber, polymer, composite, fiberglass, and combinations thereof.

Figure 5:
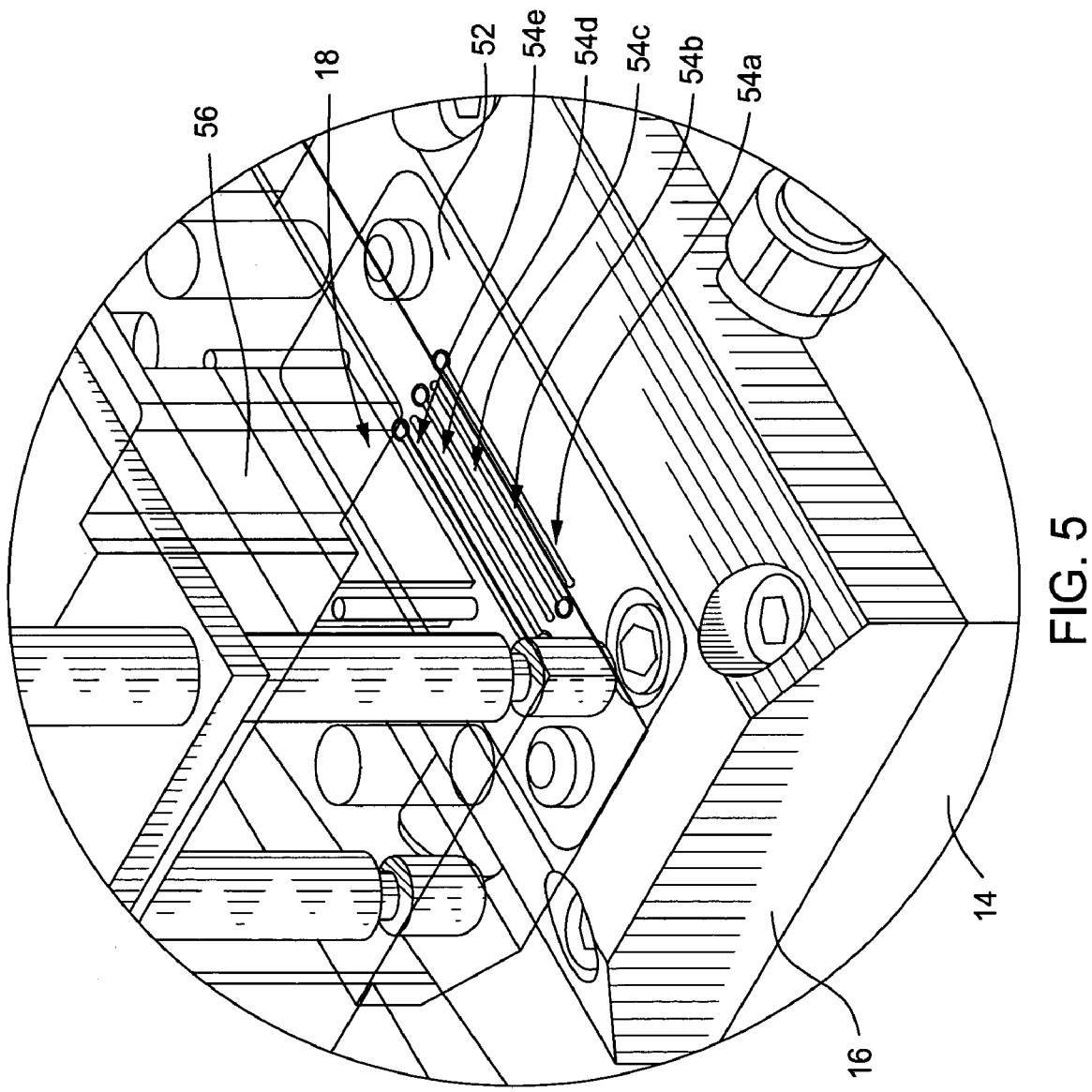
FIG. 5 is a perspective view of a portion of the apparatus shown in FIG. 1.

With reference to FIG. 5, a perspective view of a portion of the cutting apparatus 10, in accordance with the present invention is shown and includes the fiber chamber 14 and the blade receiving plate 16. In communication with the blade receiving plate 16 is the blade slot plate 52, which has blade slots 54a, 54b, 54c, 54d and 54e to accommodate the two or more cutting blades 18 attached to the cutting blade holder 56. As the two or more cutting blades 18 move toward the blade slot plate 52, the two or more cutting blades 18 pass through the fibers (not shown) and pass into the blade slots 54a, 54b, 54c, 54d and 54e. The cut fibers (not shown) fall into the slots 54a, 54b, 54c, 54d and 54e and accumulate in the fiber chamber 14. The number of cutting blades 18 will depend on the preference of the user and the physical constraints of the cutting apparatus 10. For example, the cutting apparatus 10 includes 2, 3, 4, 5, 6, 7, 8, 9, 10, 11, 12, 13, 14, 15, 16, 17, 18, 19, 20 21, 22, 23, 24, 25, 26, 27, 28, 29, 30 or even more than 30 cutting blades The cutting apparatus 10 can be individually constructed either in part or entirely of a metal, an alloy, a plastic, a polymer, a carbon nanotube, fiberglass, a composite, graphite, stone, wood or other suitable materials or a combination thereof. Furthermore, the cutting apparatus 10 may be automated through the use of a computer, network system or CPU. The automation may control the air pressures, the cutting pressure, the timing of the cutting and transporting of the fiber.

The present invention includes an image-processing algorithm for analyzing longitudinal images of fibers (e.g., cotton) in an automatic system, having improved accuracy and efficiency. The adaptive thresholding of the present invention reduces the errors arising from unfocused fibers and the lookup table increases the efficiency of tracing fiber edges. A double-scanning algorithm enhances the accuracy of transverse scans of fibers, while the validation rules prevent false scans from being included in the output. A merging algorithm links short segments that belong to the same fiber so that fiber twists can be evaluated.

Cotton properties are measurable from the microscopic images of cotton fibers captured in both longitudinal and cross-sectional views [1-9]. To take longitudinal measurements, fibers are usually cut into short segments/snippets, spread on a glass slide, and imaged by a video camera through a light microscope at the magnification of approximately 450× and range from 300×-600×. Due to inherent variability of cotton, a reliable prediction of any cotton properties must be based on the measurements of a large number of fibers. Thus, the sample slide needs to be automatically transported on the microscope to permit as many fibers as possible to be imaged at different positions. The movements of the slide make it difficult to keep all the images well focused. Fibers with fuzzy edges may cause errors in fiber width measurements because locating appropriate edges of a fuzzy fiber is problematic. Fibers often cross or touch each other, and measurements taken at a joint of two fibers can seriously distort the width data of these two fibers. Since cotton fibers are convoluted, the edges of fibers is often heavily curved, this adds errors to the estimation of the scanning directions across the fibers. The accuracy of the measurement is also dictated by other problems, such as merging scanned segments belonging to the same fiber. The present invention uses algorithms that deal with these problems to develop a reliable and efficient imaging system for measuring cotton fineness and maturity from longitudinal views.

Figure 6:
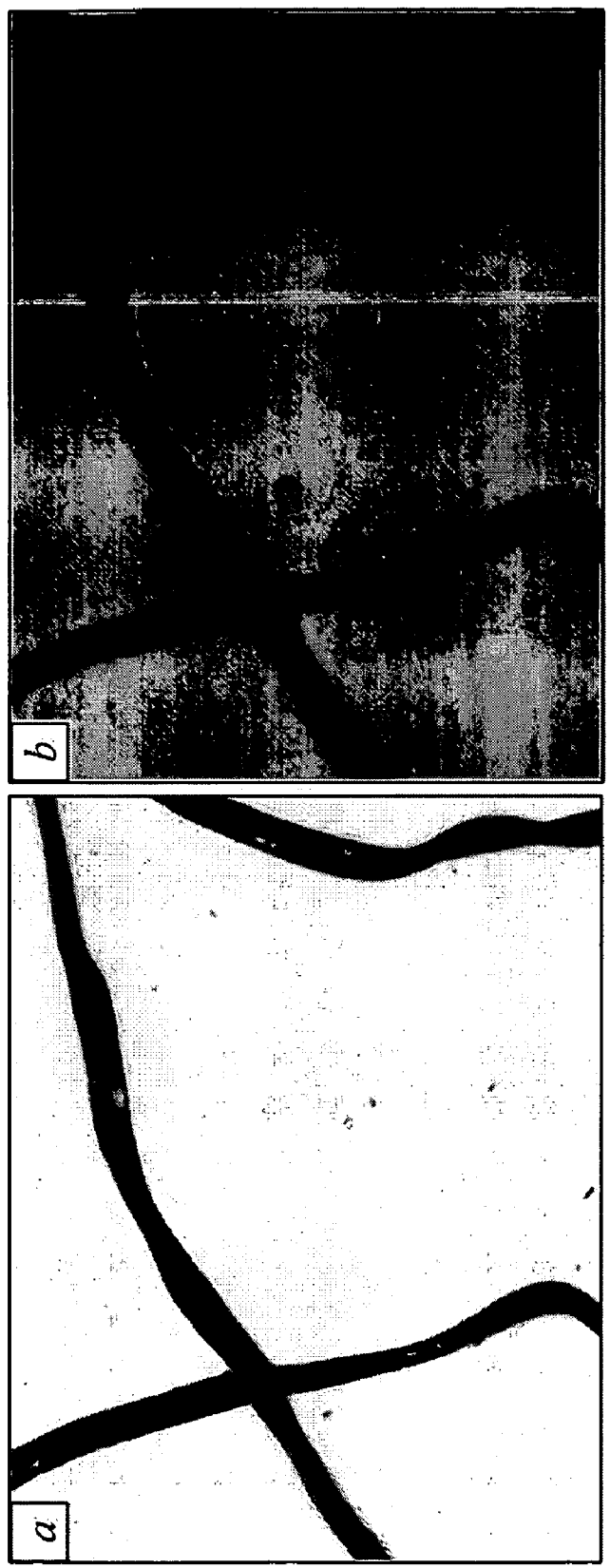
FIGS. 6A and 6B are images using different focusing and lighting conditions.

Adaptive Thresholding. A fiber image taken by a CCD camera under a transmitting light source can be formatted to an 8-bit bitmap that has grayscales from 0 (black) to 255 (white). In the image, the area covered by fibers has significantly lower grayscales than the unblocked area, and pixels near fiber edges have intermediate grayscales, forming a transition band between the fiber and the background. The width of the transition band varies with the lighting and focusing conditions. Fibers with fuzzy edges have much wider transition bands, which create problems in identifying fiber edges correctly. FIG. 6 illustrates two images of the same fibers with different focusing and lighting conditions. Fibers in FIG. 6B appear much coarser than those in FIG. 6A, although physically they are identical. To ensure reliable geometrical measurements of fibers, fibers in a grayscale image must be reasonably and consistently identified regardless of the image capturing conditions.

Thresholding an image is a process to separate objects from the background by using a criterion to sort every pixel in the image. A threshold can be simply calculated based on the average brightness of the image and applied to the entire image. FIG. 6A illustrates the mean threshold is appropriate when the image is sharp and the background is bright, whereas FIG. 6B tends to overestimate unfocused fibers in a dark image. In FIG. 6A the average width of the fibers is 1.44 times larger than that the fibers in FIG. 6B when the images are thresholded using the mean values. The reason for overestimating fibers in an unfocused image with the mean value is that pixels in transition bands have much lower grayscales than the mean value, and are all classified as fibers pixels. The mean grayscale of an image does not correspond to the realistic edges of unfocused fibers.

The threshold is dynamically adjusted to compensate for changes in the focusing and lighting condition that can be reflected in the histogram of the image. A histogram is a distribution of the pixels against the grayscale, revealing allocations of pixels belonging to the fibers and background. The histograms of the two images in FIG. 6 are presented in FIGS. 7A and 7B.

Figure 7A:
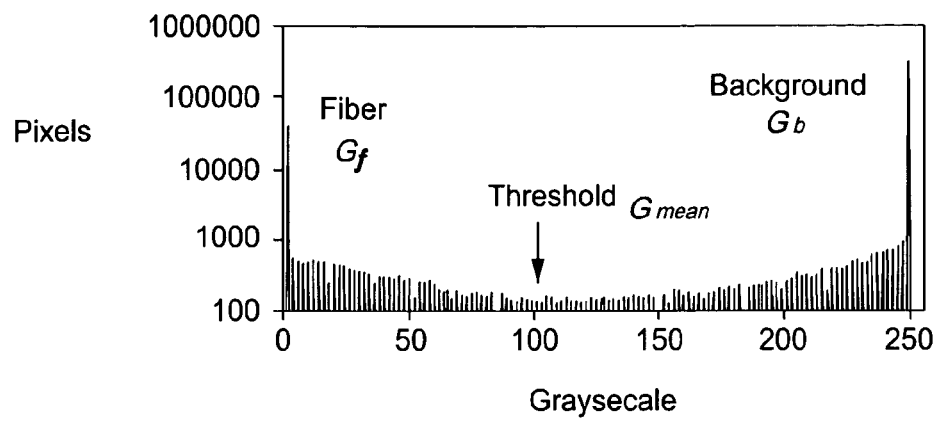
FIGS. 7A and 7B are histograms of the respective images in FIG. 6.

As shown in FIG. 7A, the histogram of the sharp and bright image in FIG. 6A has two distinct peaks that appear at the two ends of the grayscale and the pixel counts decrease towards the center of the grayscale gradually. The two peaks correspond to the major portions of the fiber and background pixels ($G_f$ and $G_b$), and the distributions between the two peaks are dictated by transition bands of fiber edges and variations in background. In this case, the mean grayscale ($G_{mean}$) seems to be an optimal threshold that separates the fibers and the background.

Figure 7B:
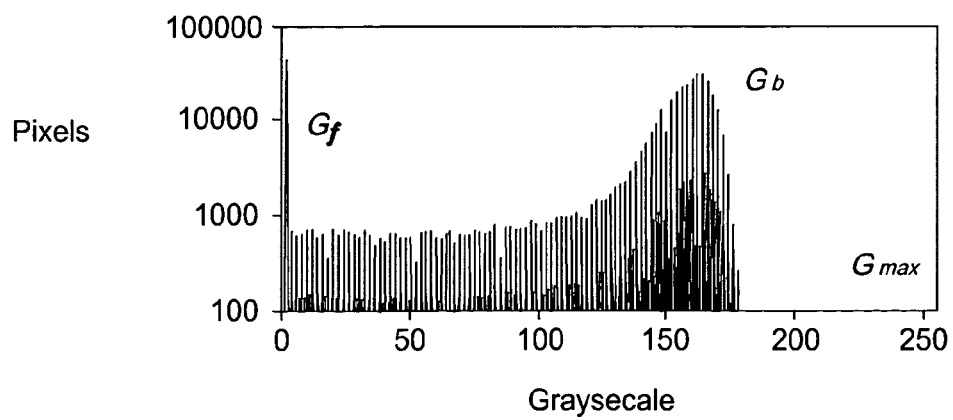

FIG. 7B shows the histogram of the image in FIG. 6B. It can be seen that when the image is dark and out of focus, the valid range of the histogram is compressed and the change in distributions occurs unevenly in the fiber and background regions. The histogram compression moves much more pixels into the fiber peak so that fibers are more likely to be overestimated when the mean grayscale $G_{mean}$ is used as a threshold. Therefore, the new threshold should be formed by adjusting $G_{mean}$ with the valid range of a histogram. For the unfocused image (e.g., FIG. 11B), the valid range of the histogram was decreased (e.g., $G_{max}$–$G_b$), and the threshold may be calculated. The coefficient c can be experimentally determined. In one example, a value around 2.0 was found to be effective for the coefficient.

Figure 8B:
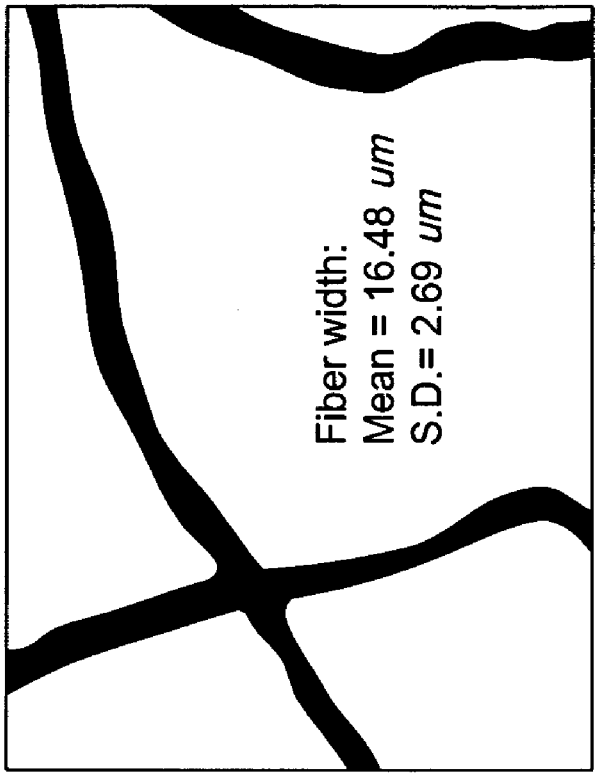
FIG. 8 is an image of adaptive thresholding of the images of the present invention as seen in FIG. 6.
Figure 8A:
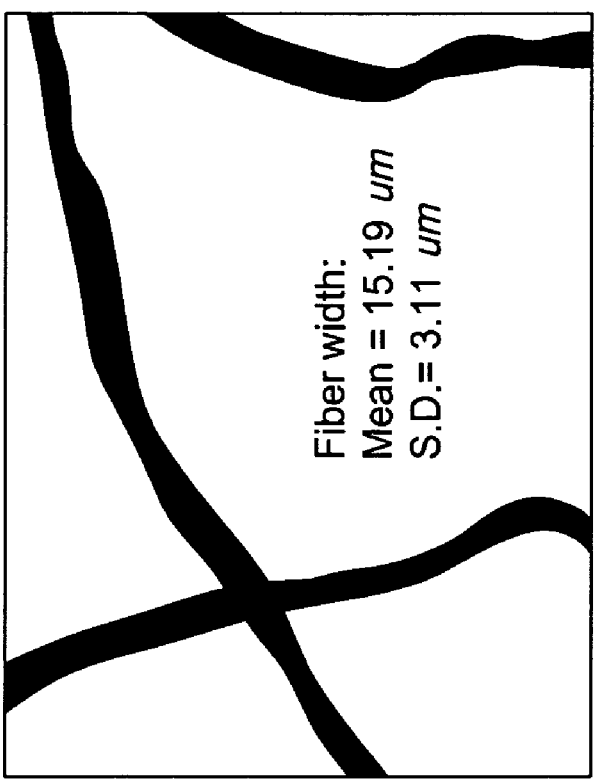

FIG. 8 shows the binary images of the original images in FIG. 6 using adaptive thresholding method. The two binary images become much more consistent even though the corresponding grayscale images are captured under very different focusing and light conditions. The average width of the unfocused and dark fibers is about 1.08 larger than that of the focused and bright fibers.

Figures 9, 10:
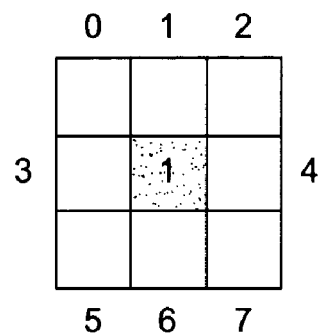
FIG. 9 depicts the numbering of neighboring active pixels.
FIG. 10 depicts invalid codes for the neighboring active pixels.

Edge Tracing. To measure the widths of the fibers, the fibers need to be scanned from edge to edge transversely. Edge tracing is a step to identify the edge pixels of fibers for the transverse scanning. To present a binary image, a "1" is used to stand for a black pixel (fiber) and "0" for a white pixel (background); although other designations may be used. When a black pixel is located, the algorithm determines whether it is an edge pixel, and if so, what are the increments in the x and y directions for locating the next edge pixel. The judgment can be made from the presence of the eight neighbors of this active pixel (e.g., FIG. 9). There are 256 possible combinations regarding the presence of the eight neighbors. As shown in FIG. 9, a ranking number from 0-7 is assigned to the adjusent neighbors.

A code representing the neighbors of the current pixel can be calculated with the statuses and ranking numbers of the eight neighbors: where $P_i$ is a binary variable indicating the presence status of the $i^{th}$ neighbor. $P_i=1$ when the $i^{th}$ neighbor is a black or fiber pixel, otherwise $P_i=0$. For each code, one can analyze the available neighbors around the active pixel and determine if this pixel is an edge pixel and which neighbor should be traced next. The 256 codes and the corresponding neighboring situations constitute a look-up table that provides a quick solution to the computer when it traces fiber edges. Some pixels are noise on the edge (e.g., a small branch or a short bridge) and are not traced with the corresponding codes should not be included in the look-up table.

FIG. 10 provides some examples of the invalid codes when the current pixel is bounded with 1 to 4 isolated black pixels or surrounded by all eight neighbors. The first four codes in the figure represent cases where the current pixel and its neighbors form branches (e.g., codes 1 and 5), bridges (e.g., codes 49 and 165) and the last code (e.g., 255) indicates a non-edge pixel because the active pixel is encompassed by all black pixels. In instances where the code represents a valid edge pixel, the algorithm finds the next pixel and the x and y increments from the active pixel. Since the increments are direction dependent, four separate look-up tables can be created based on the four tracing directions: up-right, up-left, down-right or down left.

Figure 11:
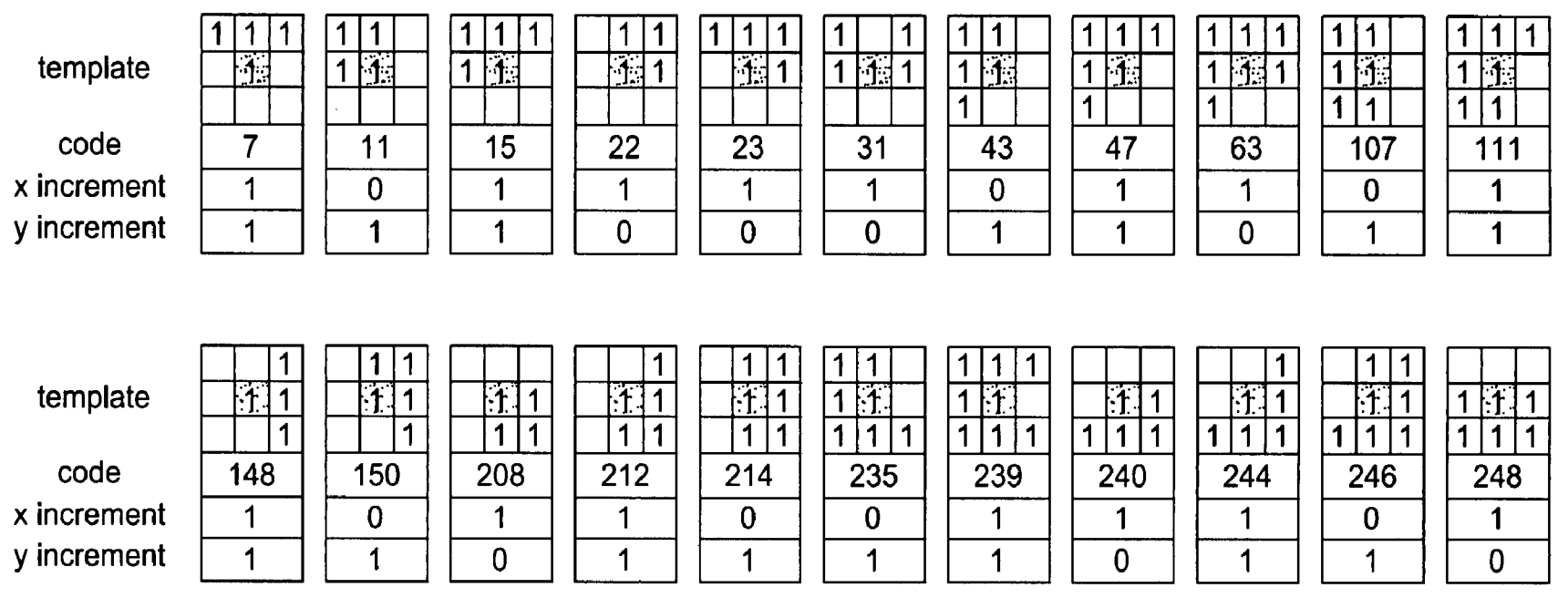

FIG. 11 shows the valid codes in the look-up table in the up-right direction. One code in this table indicates that a new edge pixel can be traced from the active position in this direction, and the x and y increments are given by the relative position of the new pixel. In some cases, a pixel may have multiple neighbors that can be followed in the tracing direction (e.g., code 31 in the up-right direction). The next neighbor to be traced is chosen in the counterclockwise order. In instances where the neighbors around the active pixel do not match any of these templates, a look-up table in another direction is called for further comparisons. The current tracing is terminated if the validity checking from the four look-up tables is false.

Figure 12:
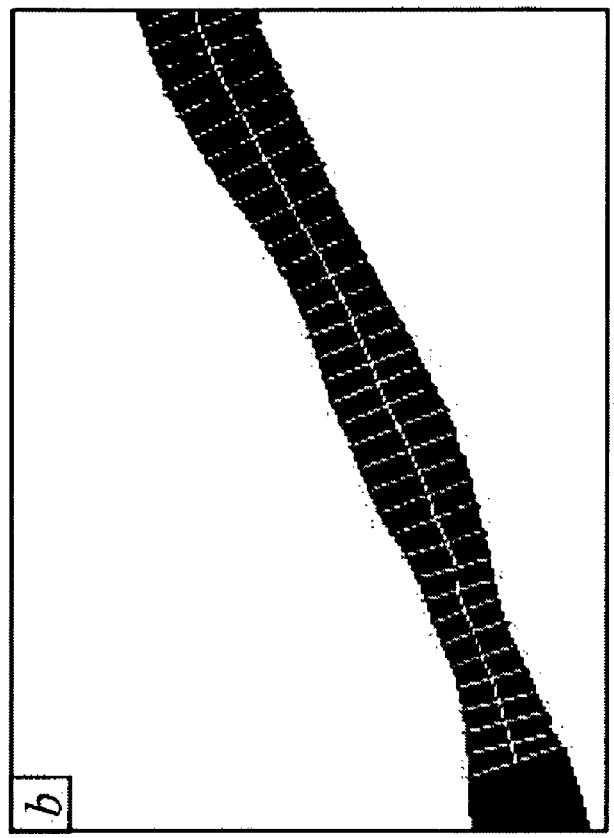
FIG. 12 is a transverse scanning image in accordance with the present invention.
Figure 12:
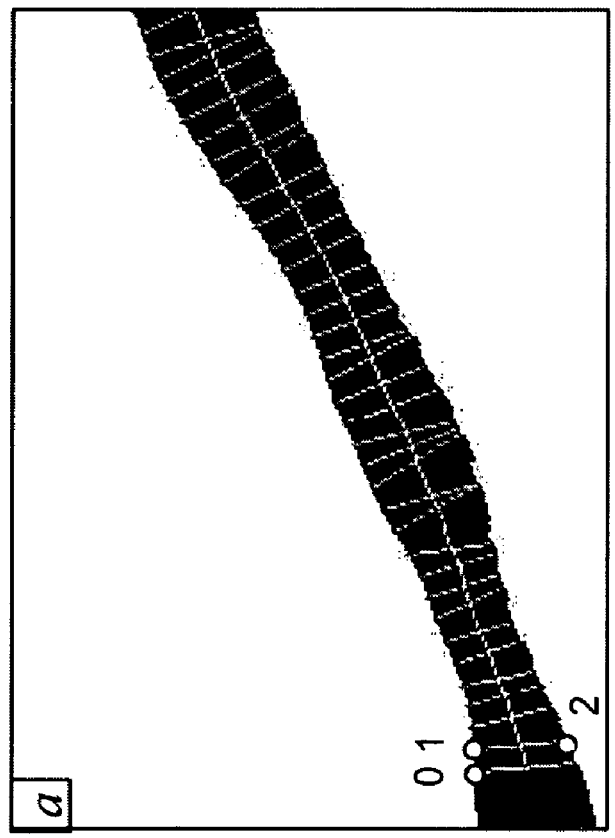

Transverse Scanning. Transverse scanning is a step to determine the fiber width at an edge point in a direction perpendicular to the edge of the fiber. To conduct transverse scanning along a fiber, an interval that controls the spacing of two consecutive scans must be given and the direction of the fiber edge at a scanning point needs to be estimated. FIG. 12A illustrates a current edge pixel as $0(x_0, y_0)$ and the next edge pixel $1(x_1, y_1)$. The distance between $0(x_0, y_0)$ and $1(x_1, y_1)$ is equal to the scanning interval. The edge direction at $1(x_1, y_1)$ can be approximated by the slope of the line connecting these two pixels. The transverse scanning starts at $1(x_1, y_1)$ and follows a direction perpendicular to the calculated edge direction until it meets an edge pixel $2(x_2, y_2)$ on the other side of the fiber. The distance between $1(x_1, y_1)$ and $2(x_2, y_2)$ is a local measure of the fiber width. FIG. 12A shows the transverse scanning at a 10-pixel interval. Since cotton fibers are convoluted, the edges of fibers are often curved. The calculated directions at some scanning pixels may not realistically indicate the edge directions causing errors in the width measurements, which can be reduced by rescanning the fiber using the directions calculated from its axis. After the initial scanning, the middle points of all the scans are connected, and the direction perpendicular to the middle axis at each middle point is used to search for edge pixels on both sides of the axis. It can be seen from FIG. 12B that the line connecting two middle points gives a direction that more precisely represents the local directions of both sides of the fiber. The double scanning algorithm also generates much more uniform scans on both sides of the fiber.

Figure 13:
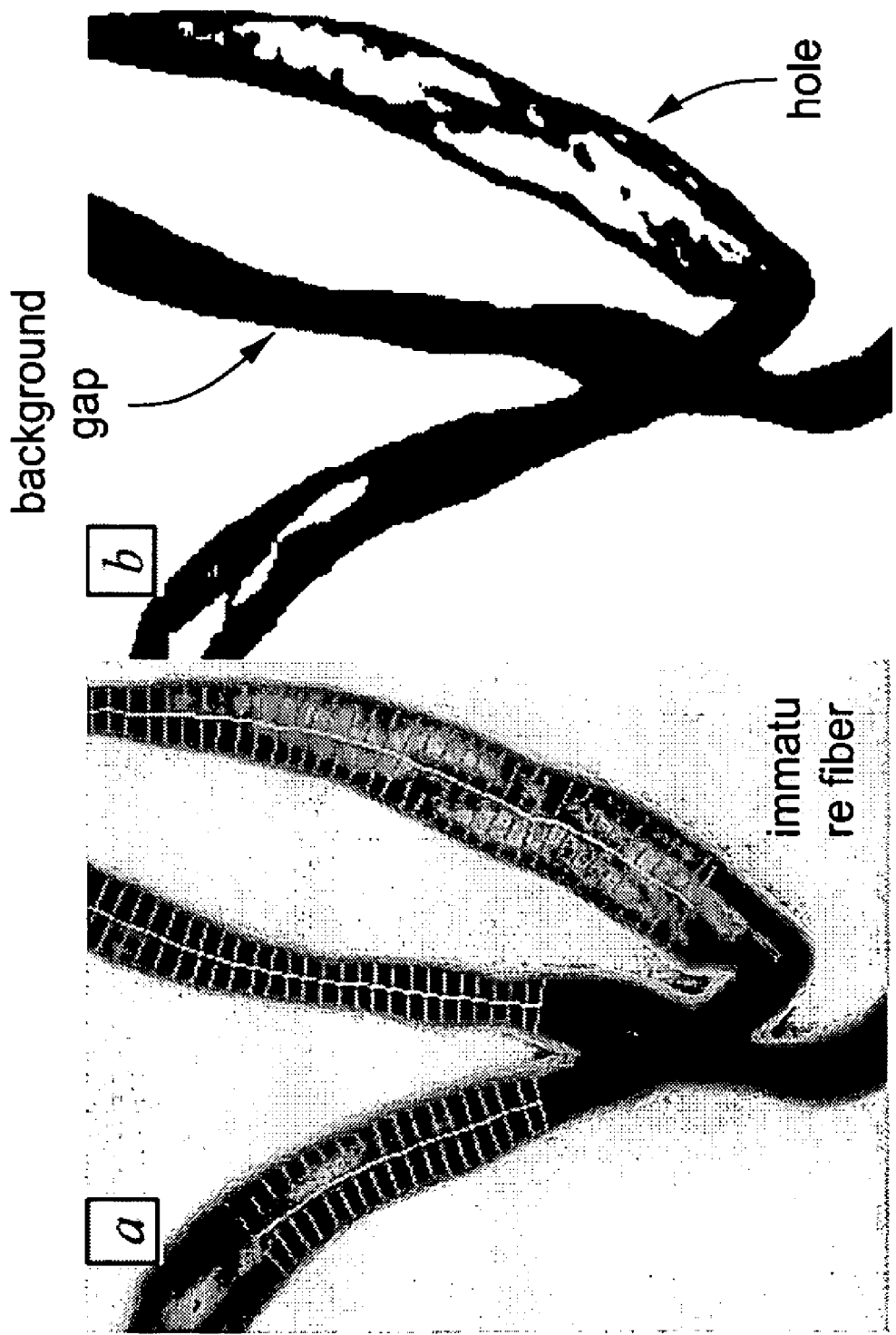
FIG. 13 is a transverse scanning image of immature fibers.

When immature cotton fibers exist in the image, the transverse scanning must deal with gaps of various sizes within fiber regions. Immature fibers have thinner walls and therefore are more transparent than mature fibers as seen in FIG. 13A. After thresholding, the bright portions in the immature fibers may become holes (e.g., white pixels) in the binary image. In order to discern holes within a fiber from background gaps between fibers, the grayscale information of those areas in the original image must be used. As shown in FIG. 13A, the grayscale of immature fibers are differentiably lower than the background. If a discontinuity occurs during the transverse scan on the binary image, the corresponding pixel in the original image is checked. If the grayscale is lower than the background ($G_b$), the pixel is considered as fiber holes and the scanning continues. The transverse scans over the immature fiber were also shown in FIG. 13A. The detection of these highly transmissive regions is particularly useful for identifying dead cotton fibers.

Figure 14:
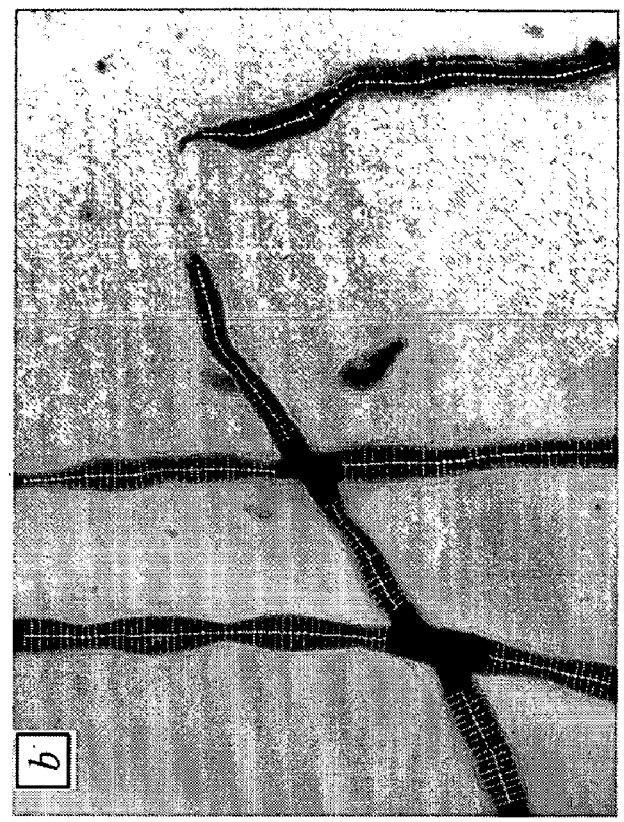
FIGS. 14A and 14B are transverse scanning images in accordance with the present invention, where
Figure 14:
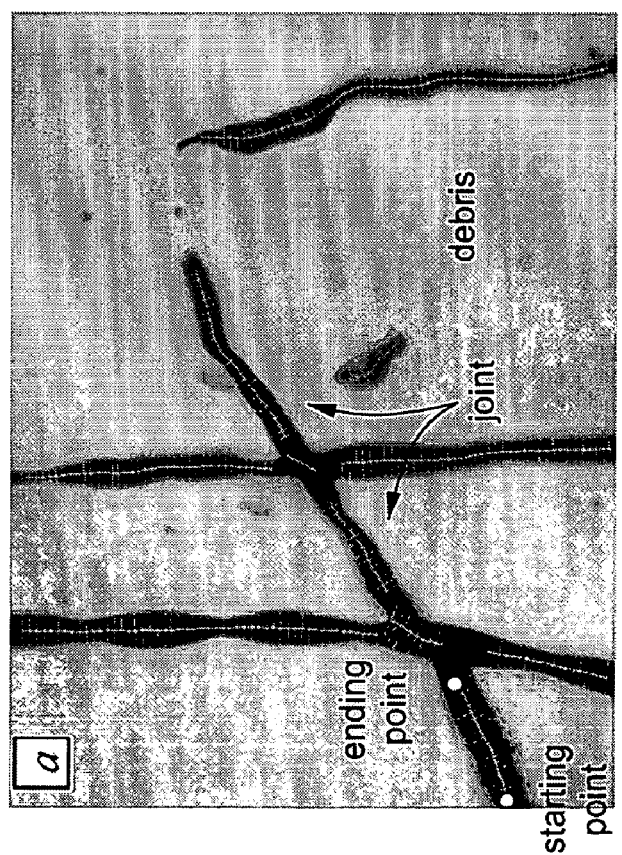

Scan Validation. Validation is a step to avoid or remove improper scans during or after the transverse scanning. Improper scans are those on various debris and intersections of two or more fibers as seen in FIG. 14A. Since fibers may intercept each other at any angle, crossing detections need to be conducted at multiple stages. During the scanning, each scan is examined with the following rules:

(1) The length of the scan should not exceed the preset limits for the minimum and maximum widths of cotton fibers. In one example, the lower and upper limits were set to 3 μm and 65 μm, respectively. The two limits give a sufficient range for valid cotton widths, but exclude scanning on extremely small or large objects in the image.

(2) The length difference between two consecutive scans should not exceed 50%. A sudden change in scan length suggests a joint of another object to the current fiber.

(3) The direction change between two consecutive scans should not exceed 20°. A sudden change in scan direction also suggests a crossing point with another fiber.

If a scanning procedure violates one of these rules, it will be terminated. A new scanning procedure starts at the next valid edge pixel. Because of the interruptions, a fiber may have multiple scanned segments of various lengths. The starting and ending points of each segment are registered. After the entire image is processed, all the scans are further checked to find fiber crossing regions and short debris undetected during the scanning with the following rules:

(1) The coefficient of variance (CV) of the scan lengths of one scanned segment should not exceed 0.65. When the CV of a segment is higher than 0.65, the segment is considered having too large variations in scan width that may be caused by touching or crossing sections of two objects.

(2) The length of one scanned segment should be three times larger than the average width of the segment. Thus, scans on short debris can be deleted.

If a scanned segment violates either rule, all the scans in that segment are deleted. FIG. 14B presents transverse scans of fibers after applying these validation rules to FIG. 14A, demonstrating that the validation is crucial for improving the accuracy of the data.

Merging. One of the important tasks to be done in the longitudinal analysis is to assess the maturity of cotton fibers based on the fiber convolutions [2, 4]. To analyze the longitudinal convolution, a fiber should be scanned to have multiple twists so that the adequate information about the fiber width variations can be obtained. Since the transverse scanning along a fiber may be interrupted by joints with other objects, the scanned fibers may contain several scanned segments, each of which may not be long enough to have a complete twist. Hence, separate segments belonging to the same fiber need to be connected.

Figure 15:
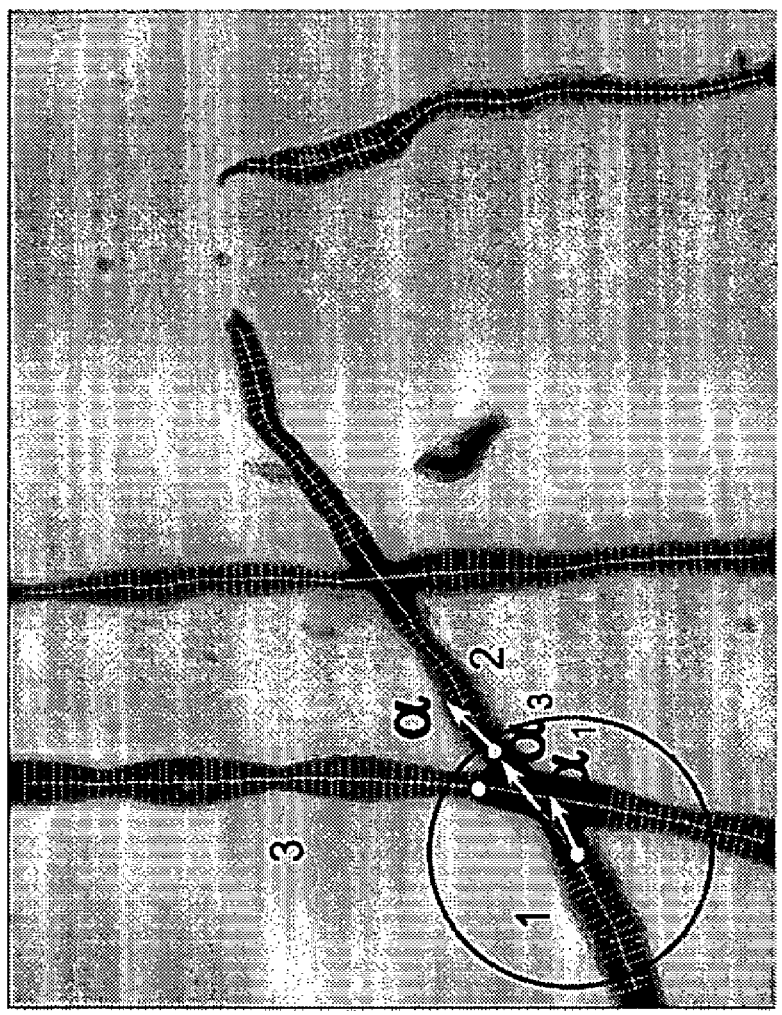
FIG. 15 is an image of the merging of a transverse scanning image over a fiber image.

In order to avoid false connections between two segments, two parameters are used to judge whether the connection can proceed. The first parameter is the distance between the ending point of the first segment and the starting point of the second segment. If the distance is within three times of the average width of the first segment, the two segments are then considered for merging. FIG. 15 shows an example of the segment merging. For the ending point of segment 1, only the starting points of segments 2 and 3 are within the given range, and therefore the candidates are for a possible connection. The second parameter is the angle between the two segments at their connecting ends. Assume that the directions of segments 1 and 2 are $\alpha_1$ and $\alpha_2$. If the difference between $\alpha_1$ and $\alpha_2$ is within a given tolerance (20°), (i.e., $|\alpha_2-\alpha_1|20°$), the connection between the segments should be forwarded. This requirement eliminates segment 3 in FIG. 15 for the connection with segment 1. The third parameter is the direction ($\alpha_3$) of the line connecting the two ends. $\alpha_3$ should be within angles $\alpha_1$ and $\alpha_2$. This requirement prevents connecting two parallel segments, which are close to each other but not from the same fiber. There are four correct connections made in FIG. 15.

One embodiment of the present invention provides longitudinal measurements of cotton fibers performed on a customized imaging system that includes a video zoom microscope, a B/W CCD camera, and a frame grabber. The imaging system can also analyze fiber cross sections. In one example, the image resolution was about 1.86 μm/pixel. A microscope was equipped with a motorized stage that automatically transports the sample slide to allow the camera to grab fiber images at many different positions. During the travel to the next position, fibers in the grabbed image were scanned and the image was discarded. The sample preparation was done with a special fiber cutter and spreader. Fibers were cut into about 0.5 mm long segments, and then randomly spread on a microscope slide.

The present invention also includes a software package to implement the algorithms. In one embodiment, the algorithm calculates the number of scans ($N_s$), the length of the scanned segments ($L_s$), the maximum ($W_{max}$), minimum ($W_{min}$), mean ($W_{mean}$) and standard deviation ($W_{sd}$) of fiber widths, and the number of twists ($N_t$) for each scanned fiber. $N_t$ is counted by the alternations of the maximum and minimum widths along a fiber axis. After the scanning of an entire slide, the software can output the statistics and distributions of all the data. The number of the scanned fibers ($T_f$), varying from 1000-4000, depends on the density of fiber segments spread on the slide. These outputs provide direct measurements for both fiber fineness and maturity of the analyzed samples.

Figure 16A:
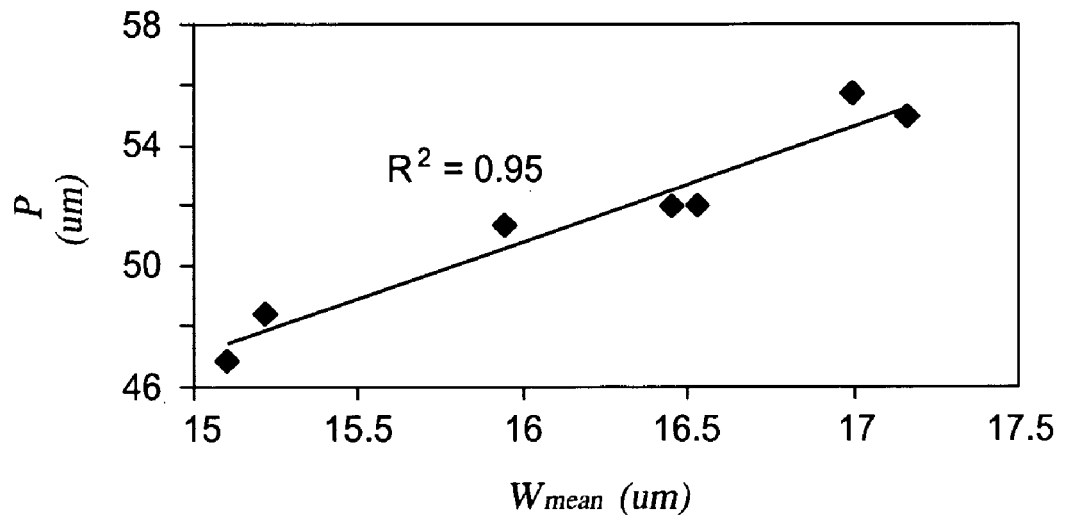
Figure 16B:
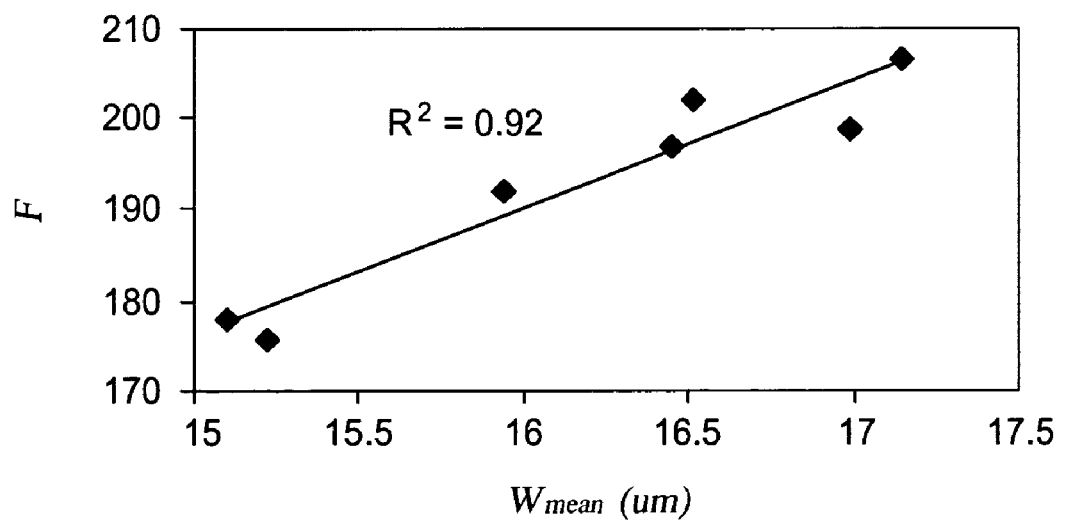
FIG. 16B is a plot of the longitudinal data using AFIS data.

For example, seven varieties of cottons were tested by the imaging system for both longitudinal and cross-sectional measurements, and by the Advanced Fiber Information System (AFIS). FIG. 16 shows the correlation of the average width ($W_{mean}$) and the average perimeter of cross sections (P) of the cottons, and the correlation of the average the $W_{mean}$ with the AFIS fineness data (F). Both analyses prove reasonable correlations among these methods.

Figure 17:
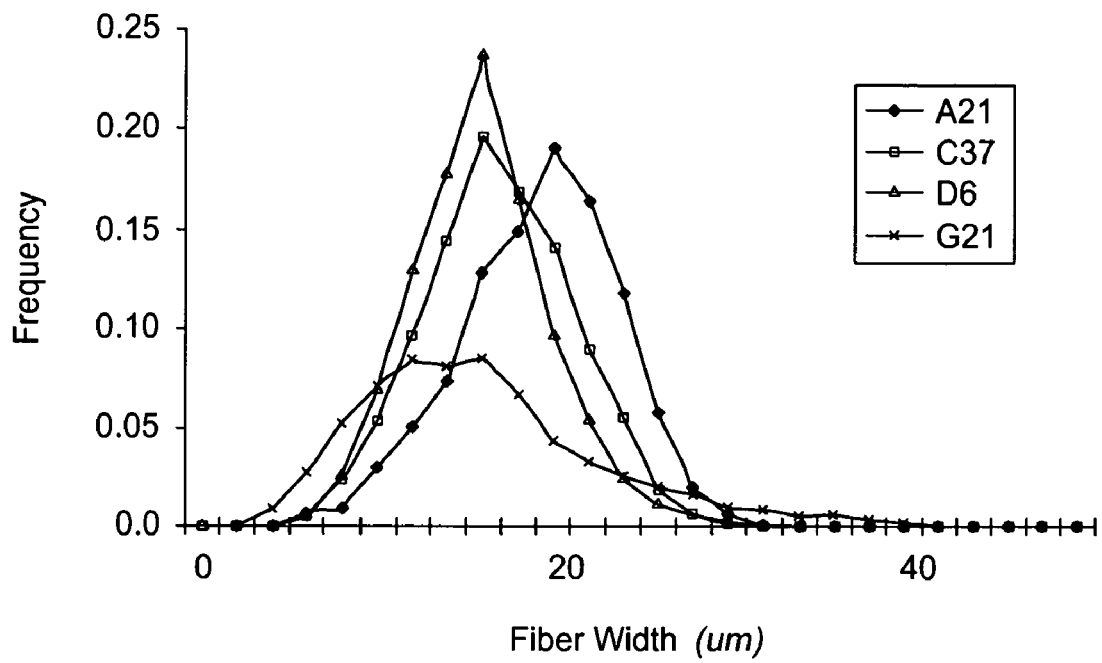
FIG. 17 is a plot of the distributions of fiber widths.

Since the imaging system can produce a large quantity of transverse scanning data from one slide, reliable distributions of fiber widths can be calculated. FIG. 17 shows the distributions of fiber widths of the four international-calibration-standard cottons labeled as A21, C37, D6 and G21. D6 and G21 have similar mean widths, but width distributions are significantly different. G21 has a much broader distribution and therefore a larger variance than D6 as G21 contains more immature fiber than D6 because immature fibers have higher convolutions. A21 and C37 have similar distribution shapes but different peak locations. Statistically, A21 is more coarse than C37.

The repeatability of the data generated from the algorithm of the present invention was tested by repeatedly scanning a sample slide under the same condition. The coefficient of variance (CV) of the data from multiple tests was used to evaluate the repeatability. Table I gives the data of a sample slide that was scanned six times. The CVs of the data from different tests are under about 4.5%, which demonstrates a good consistency of the data. Since the scanning of each test can not be started exactly at the same position on the sample slide, the images grabbed in different tests contained different portions of fibers, and the CVs might be originated primarily from the inherent variations of fibers.

TABLE I

| Test | $T_f$ | $N_s$ | $L_s$ (um) | $W_{max}$ (um) | $W_{min}$ (um) | $W_{mean}$ (um) | $W_{sd}$ (um) | $N_t$ |
|---|---|---|---|---|---|---|---|---|
| 1 | 1669 | 50.23 | 171.89 | 19.46 | 10.92 | 15.25 | 4.44 | 2.25 |
| 2 | 1694 | 50.30 | 171.94 | 18.81 | 10.42 | 14.67 | 4.41 | 2.36 |
| 3 | 1743 | 51.83 | 178.74 | 19.04 | 10.44 | 14.76 | 4.43 | 2.34 |
| 4 | 1715 | 53.40 | 184.67 | 19.02 | 10.27 | 14.70 | 4.52 | 2.38 |
| 5 | 1576 | 52.44 | 180.13 | 18.81 | 9.98 | 14.82 | 4.56 | 2.54 |
| 6 | 1593 | 52.56 | 179.34 | 19.06 | 10.17 | 14.67 | 4.57 | 2.44 |
| CV (%) | 4.03 | 2.49 | 3.12 | 1.40 | 3.27 | 1.59 | 1.46 | 4.41 |

In another example, a test on a bale of cotton was conducted to investigate the level of variability of the longitudinal data across the cotton bale through multiple samplings, and to find out how many fibers need to be scanned so that the data are sufficient and reliable for estimating the attributes of the whole bale. A total of 25 samples were taken from the bale at different places, and three slides were prepared for each sample. Table II shows the results of the 25 samples. For one sample, each measurement in the table is the average of all fibers on three slides. Due to the difficulty in controlling the densities of fibers on the slides, the total number of scanned fibers ($T_f$) for a sample varied greatly, which in turn influences the number of scans ($N_s$) the scanned length ($L_s$), and the number of twists ($N_t$) on single fibers. Thus, the CVs of these four parameters do not solely reflect the variability of cotton. However, the CVs of the four width measurements, $W_{max}$, $W_{min}$, $W_{max}$ and $W_{sd}$, more closely link to the variability of cottons, and they are significantly higher than those of fibers on one slide.

TABLE II

| Sample | $T_f$ | $N_s$ | $L_s$ (um) | $W_{max}$ (um) | $W_{min}$ (um) | $W_{mean}$ (um) | $W_{sd}$ (um) | $N_t$ |
|---|---|---|---|---|---|---|---|---|
| 1 | 9438 | 42.19 | 146.43 | 20.57 | 12.22 | 16.24 | 4.32 | 2.01 |
| 2 | 9586 | 41.55 | 144.51 | 20.35 | 12.08 | 16.06 | 4.24 | 2.01 |
| 3 | 5840 | 46.78 | 162.75 | 19.62 | 11.04 | 15.21 | 4.43 | 2.25 |
| 4 | 6202 | 49.48 | 171.92 | 19.60 | 10.82 | 15.06 | 4.51 | 2.37 |
| 5 | 4918 | 50.17 | 172.36 | 19.68 | 11.33 | 15.34 | 4.18 | 2.42 |
| 6 | 6825 | 46.43 | 160.62 | 19.38 | 10.96 | 15.05 | 4.36 | 2.24 |
| 7 | 6354 | 49.19 | 170.24 | 19.86 | 11.32 | 15.51 | 4.39 | 2.26 |
| 8 | 9080 | 44.97 | 156.45 | 20.21 | 11.69 | 15.86 | 4.42 | 3.04 |
| 9 | 7157 | 48.58 | 169.30 | 19.36 | 10.80 | 14.93 | 4.38 | 2.40 |
| 10 | 7213 | 47.27 | 163.38 | 19.39 | 11.07 | 15.12 | 4.27 | 2.31 |
| 11 | 7770 | 47.15 | 163.62 | 19.63 | 10.95 | 15.22 | 4.49 | 2.26 |
| 12 | 5280 | 48.89 | 169.33 | 19.42 | 10.85 | 15.03 | 4.40 | 2.34 |
| 13 | 6993 | 46.80 | 161.92 | 19.83 | 11.26 | 15.37 | 4.38 | 2.26 |
| 14 | 6311 | 49.83 | 172.06 | 19.46 | 10.74 | 15.05 | 4.48 | 2.46 |
| 15 | 7302 | 42.84 | 149.58 | 19.11 | 10.84 | 14.84 | 4.29 | 2.18 |
| 16 | 6883 | 44.83 | 156.31 | 18.95 | 10.83 | 14.80 | 4.23 | 2.19 |
| 17 | 7262 | 47.83 | 165.99 | 19.30 | 10.69 | 14.91 | 4.45 | 2.33 |
| 18 | 7600 | 44.87 | 156.23 | 18.99 | 10.82 | 14.76 | 4.24 | 2.23 |
| 19 | 6908 | 48.35 | 166.72 | 19.96 | 11.19 | 15.45 | 4.51 | 2.25 |
| 20 | 7984 | 46.57 | 162.10 | 19.68 | 11.23 | 15.35 | 4.31 | 2.25 |
| 21 | 6973 | 46.89 | 162.48 | 19.58 | 11.11 | 15.21 | 4.34 | 2.32 |
| 22 | 6832 | 47.12 | 164.38 | 19.33 | 11.06 | 15.07 | 4.21 | 2.26 |
| 23 | 8758 | 44.01 | 152.94 | 18.97 | 10.79 | 14.78 | 4.25 | 2.15 |
| 24 | 6388 | 45.99 | 160.05 | 20.18 | 11.77 | 15.82 | 4.29 | 2.13 |
| 25 | 5159 | 43.65 | 152.46 | 20.68 | 12.11 | 16.28 | 4.37 | 2.21 |
| CV (%) | 17.31 | 5.13 | 4.90 | 2.41 | 4.04 | 2.91 | 2.23 | 8.37 |

Figure 18:
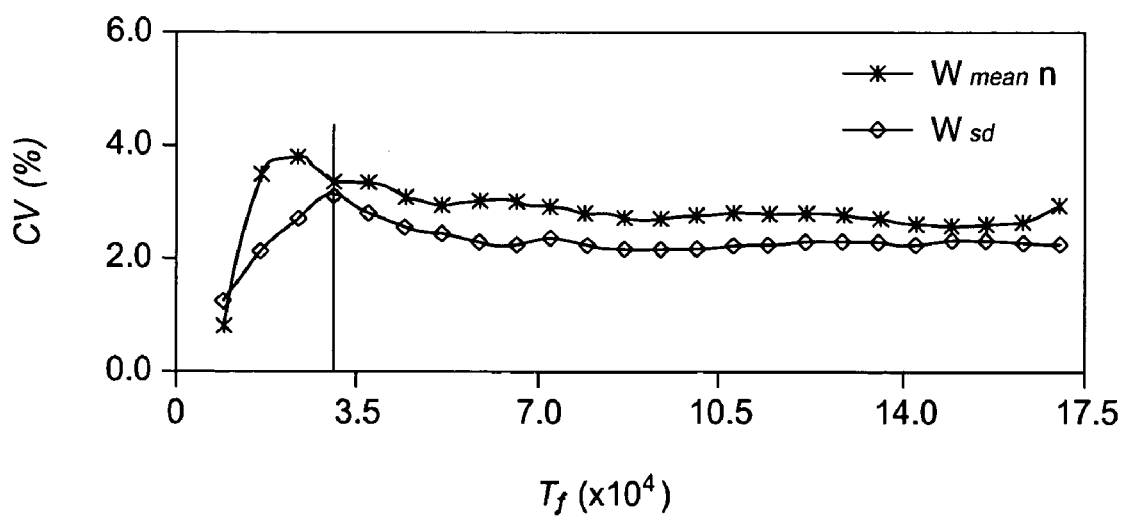
FIG. 18 is a plot of variations of fiber widths in different samples.

When the data from all the 25 samples (e.g., 177,016 fibers on 75 slides) were pooled together, the CVs of the fiber width measurements could be calculated with different numbers of fibers. FIG. 18 shows the curves of $W_{mean}$ and $W_{sd}$ against the $T_f$ of the fibers taken into account. Initially, the CV increases with the $T_f$ meaning that sampling more fibers adds information about the variability of cotton in the bale. After the $T_f$ passes $3\times10^4$, the CV tends to approach to a stable level with a much smaller scale of fluctuations. This means that increasing $T_f$ in the calculations does not increase the variability information. To overcome the variability of samples, a bale of cotton should be sampled to have at least $3\times10^4$ fibers in the calculation.

The present invention includes image-processing algorithms for analyzing longitudinal images of fibers (e.g., cotton) in an automatic system, having improved accuracy and efficiency. The adaptive thresholding of the present invention reduces the errors arising from unfocused fibers and the look-up table increases the efficiency of tracing fiber edges. The double-scanning algorithm enhances the accuracy of transverse scans of fibers, while the validation rules prevent false scans from being included in the output. The merging algorithm links short segments that belong to the same fiber so that fiber twists can be evaluated.

A cross section of a fiber (e.g., cotton) contains measurable information directly related to the maturity of the fiber. Cross-sectional measurements of cotton maturity may be used as a reference when other methods need to be calibrated. Much research has been conducted using image analysis technology to measure cotton maturity and other parameters from fiber cross sections [23-25, 30-34]. The success of a cross-section method using image analysis largely relies on two techniques: fiber cross-sectioning and image segmentation. Cross-sectioning is the most important step in obtaining analyzable images of fibers. Grinding and cutting are the two general methods for fiber cross sectioning. In the grinding, a bundle of fibers embedded in a polymer resin and a hardener mixture was hardened, grinded and then polished, and the surface containing fiber cross sections was imaged on a microscope using reflected light [28]. There are many different ways of cutting a thin slice of fibers perpendicular to the long axes [20, 22]. One method of embedding cotton fibers was established by the researchers at the USDA Southern Regional Research Center (SRRC) [20, 22]. A bundle of fibers are embedded in a methacrylate medium, polymerized in a UV reactor, and cut into 1-3 µm slices with a microtome. This sectioning method greatly improves the separability and contrast of individual fibers in the image captured using transmitted light.

Image segmentation is a computational process to separate cotton cross sections from the image background and from one another. The segmentation results directly influence the efficiency and accuracy of cross-sectional measurements. Due to variations in cross-sectional shapes and in the thickness of the sliced sample, fibers in different regions may exhibit different levels of contrast and focus in an image. There are always cross sections that contact or overlap others in the image. Some appear to be damaged because of the scratching of the cutting knife. Cotton cross sections can have convex or concave boundaries, and hollow or solid cores, making many powerful segmentation algorithms, e.g., watershed segmentation, invalid for separating touching ones. The image analysis systems used for processing cotton cross-sectional images often require operator's assistances to draw separation lines between touching fibers, to locate lumens and to connect broken edges.

The present invention includes an image analysis system for fibers (e.g., cotton fibers) with an emphasis on improving the automation and accuracy of the measuring process. The present invention includes a segmentation algorithm for processing cross-sectional images and results in comparison with the fineness and maturity data obtained from the longitudinal tests and other tests. The algorithm involves a sequential of pixel manipulations specially designed for handling the problems present in a cotton cross-sectional image.

Dynamic Thresholding. In one embodiment, an 8-bit grayscale image captured by a CCD camera is used to illustrate cross-sectional features of cotton fibers. Using the cross-sectioning techniques developed by SRRC, one can get a cotton cross-sectional image similarly to the one presented in FIG. 19A, in which the illumination is rather uniform and many fibers are well separated. Because of the difference in the mounting orientations in the embedment and in maturity, some fibers in the image have inconsistent intensities on their boundaries and lumens, as shown by fibers 1 and 2 in FIG. 19A. In order to preserve the details of boundaries and lumens, the threshold used for the binary conversion of the grayscale image may be adjusted.

Figure 19:
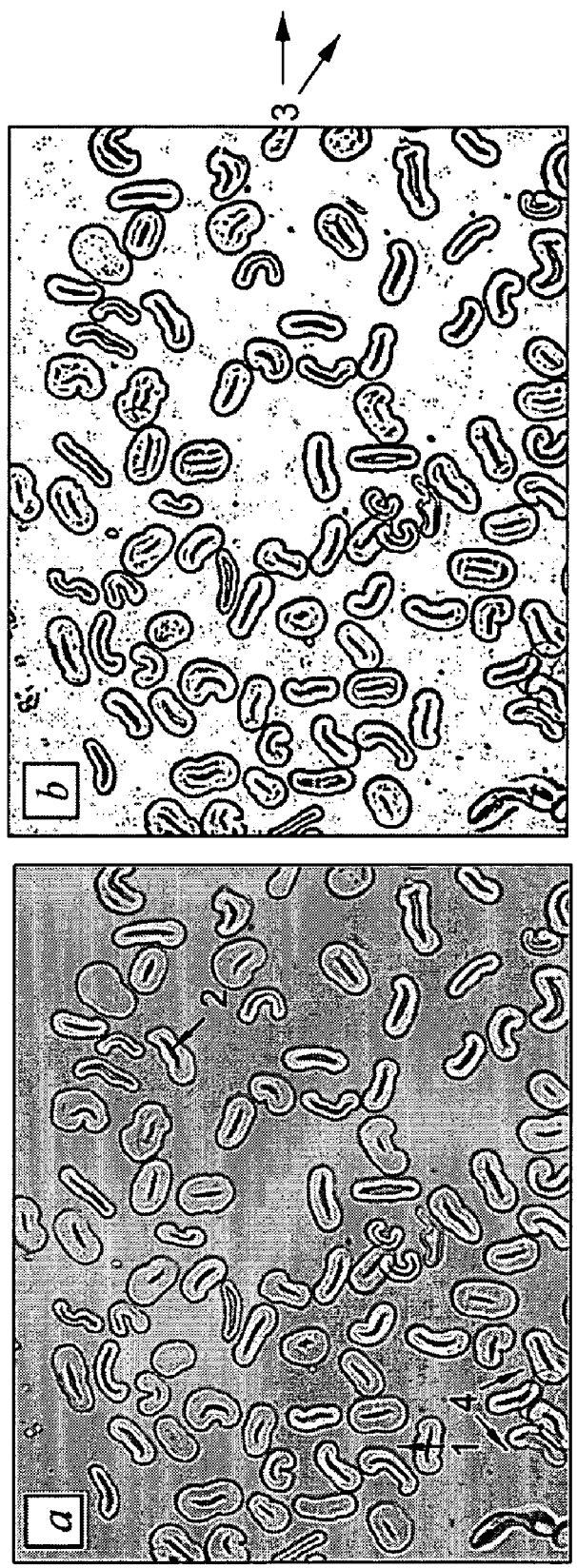
FIG. 19A is a grayscale image of the cross-section of cotton fibers.
FIG. 19B is a binary image of the cross-section of cotton fibers.

In dynamic thresholding, the image is divided into a number of sub-windows, and in each window, a local threshold is determined by the statistics of intensity values of all pixels inside the window. For the $i^{th}$ window, a simple calculation for the local threshold ($T_i$) can be achieved from the mean ($M_i$) and standard deviation ($SD_i$) of the pixel values:

$$T_i = M_i - cSD_i,$$

where c (0<c<1) is a coefficient for controlling the sensitivity of thresholding. When the intensity value of a pixel in the window is higher than $T_i$, the pixel will be set to white in the binary image, and otherwise set to black. The size of the window should be large enough to cover sufficient foreground and background pixels so that the intensities of the background pixels are above the $M_i$. FIG. 19B shows the binary image converted from FIG. 19A using a 7×7 window and c=0.2. The image preserves the details of the cross sections, including small variations inside the fiber walls and in the background.

As shown in FIG. 19B, many fibers are contacted with their neighbors, and the contacting situations depend on the shapes of the cross sections. Reasonable separations of the contacting fibers are the key to the correct measurements. With the given cross-sectioning and imaging conditions [23], a cross section always appears to have a bright cellulosic wall (e.g., secondary wall) circumscribed by the dark edges of the fiber and the lumen. The major bodies (e.g., cellulosic walls) of two contacting fibers are naturally separated by their dark edges. For these types of images, background flooding is an extremely robust way to disconnect all the touching fibers and to remove small objects in the background.

Figure 20:
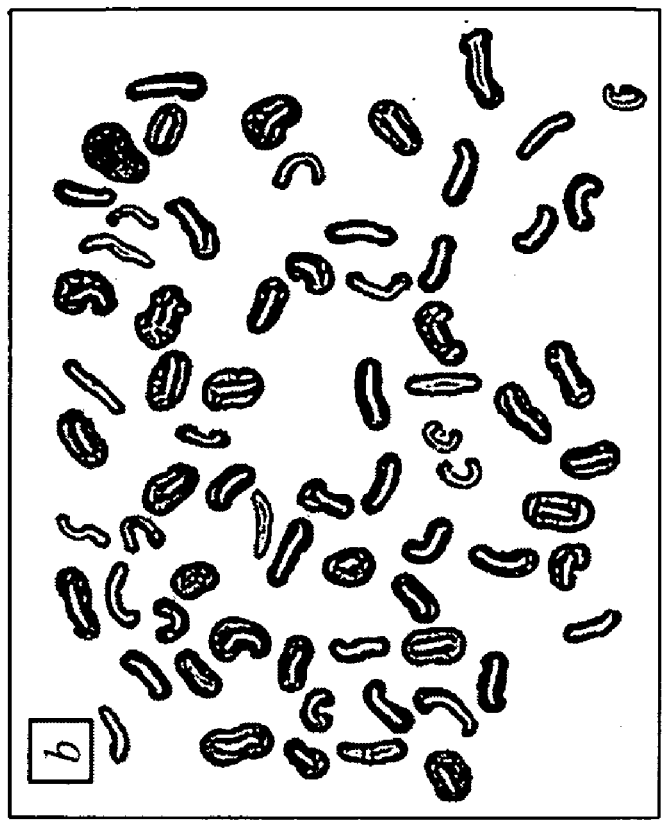
FIG. 20A is an image of fibers using background flooding and FIG. 20B is an image of fibers using partial fiber removal.
Figure 20:
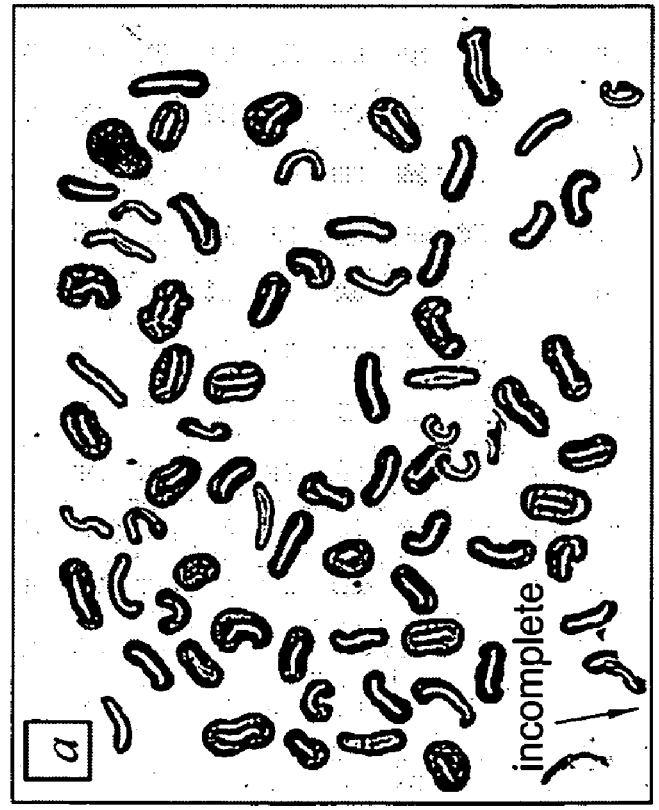

In one embodiment, the present invention, the background flooding takes advantage of a Visual $C^{++}$ function, which allows the computer to fill a region with a specified color. If the background of the binary image, as seen in FIG. 19B, is filled with the black color, all the black edges of the fibers are merged with the background, leaving the untouched inner portions in the foreground. FIG. 20A displays the inversed image of the binary image in FIG. 20B after being processed by flooding the background. Inversing the image keeps the convention that the background is in white and the foreground objects in black. Note that fibers bound with the four sides of the image (e.g., fibers labeled 3 in FIG. 20B) were automatically removed in the process to avoid incomplete fibers. Distorted cross sections arise from fibers with broken edges (see the fibers labeled 4 in FIG. 19B) because the flooding erodes the inner portions through the broken channels. Most of the incomplete cross sections can be detected by checking if they are long, thin stripes and do not enclose any hole. Besides the incomplete cross sections, this checking process also helps to remove small solid objects. In some instances, the flooding may take away the primary walls of the fibers, which are part of the dark boundaries of the cross sections. The loss of the primary walls can be compensated by adding one or more one-pixel think layers to the fiber boundaries when taking the perimeter and area measurements.

Figure 21:
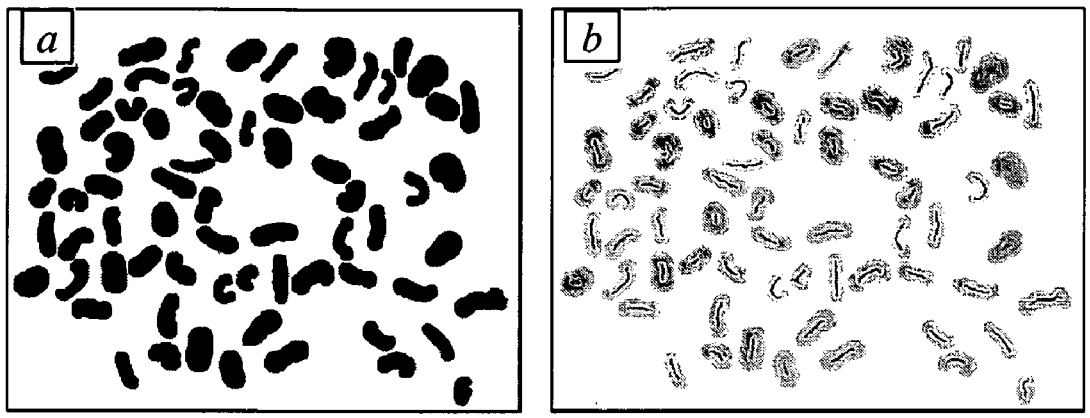
FIG. 21A is a cross section image of filled fibers and FIG. 21B is an image of skeletonized fibers.

Skeletonizing fibers to identify the fiber wall and lumen areas within each cross section. Lumens, varying in size with the degrees of maturity, are the hollow regions normally centered in the cross sections, but are often mixed with other holes, which are caused from scratching or variations in thickness of cross sections. Those holes are not counted as the portion of lumens. The medial axes or skeletons of the cross sections provide the best estimates for the locations of lumens. In order to find the skeletons, the hollow regions inside the cross sections are filled to form solid, black objects as shown in FIG. 21A.

A skeleton of a fiber is defined as a set of points where each point is at the center of the largest circle that can be fit into the object [29]. The skeletonization method used in one embodiment of the present invention involves progressive removal of the current boundary pixels from objects. The criterion for differentiating a boundary pixel from an inner pixel is that boundary pixels are only those having three or fewer black neighboring pixels. When a binary image is scanned pixel by pixel, boundary pixels are sought and registered with an intensity value in a grayscale image created in the same dimensions as the binary image. The boundary pixels are deleted from the binary image, and the modified image is re-scanned for new boundary pixels. For example, the intensity value, starting from 255, decreases with the number of iterative scans, and therefore different layers of boundaries are depicted by different grayscales. The grayscale image, referred to as a distance map, indicates the thickness of the boundary of an object to its center. As a boundary pixel is removed from the object, the number of its neighbors is also checked. If the pixel has no more than two neighbors, it will be registered with zero (e.g., black pixel) rather than the calculated value in the distance map, indicating a found skeleton pixel. The checking process is repeated until no black pixel exists in the image. FIG. 21B displays the distance map and skeletons of the fiber cross sections.

Figure 22:
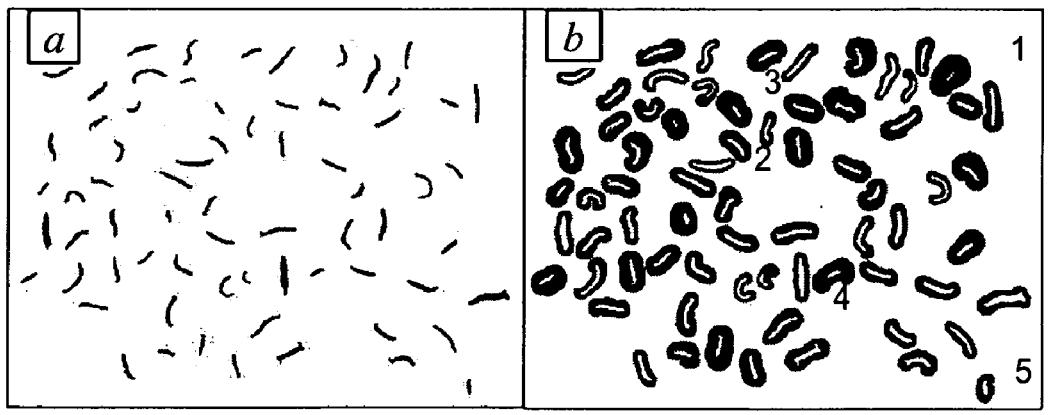

Identifying Lumens. Once the skeletons are formed, the coordinates of a skeleton are used to identify holes that fall on the skeleton of the corresponding cross section in FIG. 20B. Holes that are not passed through by the skeleton are omitted. FIG. 21A presents an image that stores all the identified lumens from FIG. 20B. The lumen image is merged with the image in FIG. 21A (e.g., filled cross-sections) using a logic calculation with which the corresponding pixels in two images are compared. In one embodiment, the logic calculation is a "XOR" operation [25, 34] used to generate a new image containing fiber cross sections with single lumens (FIG. 22B). The "XOR" operation is a logic calculation with which the corresponding pixels in two images are compared. In instances where a pair of pixels are identical, the pixel in the new image is set to "black"; otherwise, it is set to "white." The reasons for invisible lumens in some cross sections are that the fibers are either so mature that the inner spaces are fully filled or so immature that the openings are totally collapsed. In these two cases, the skeletons of the cross sections are the best estimate for the invisible lumens. Therefore, the skeletons are inserted into the cross sections, which do not possess any holes (e.g., see fibers 1, 2 and 3 in FIG. 22B). Despite all these considerations, a wrong identification of lumen may still occur (see fibers 4 and 5 in FIG. 22B) because some dead fibers are curled so severely around the long axes that their cross sections are folded into closed objects. Therefore, manual editing may be necessary to delete fibers with misidentified lumens.

Figure 23:
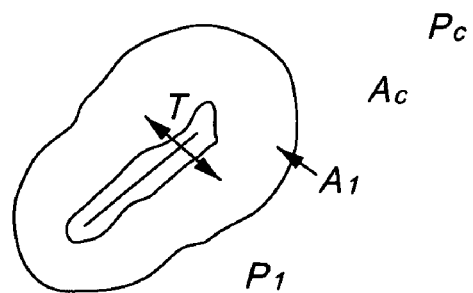
FIG. 23 is a schematic depicting the cross-sectional measurements.

Five geometric features can be directly measured for each fiber cross section, as illustrated in FIG. 23. The perimeters of a cross section and its lumen, ($P_c$ and $P_l$), are obtained by tracing the two concentric boundaries, and the areas, ($A_c$ and $A_l$), are obtained by counting all the pixels enclosed inside two the boundaries. The wall thickness at one position is measured by the pixels scanned between the boundaries in the direction perpendicular to the skeleton at this position. T is the average of the scanned thickness along the skeleton.

One embodiment of the present invention is used to describing cotton fineness and maturity using parameters derived from these direct measurements. Cotton fineness is normally described by the cotton perimeter $P_c$ and the wall area $A = A_c - A_l$, since they remain constant as the shape of the cross section changes (e.g., lumen collapse or swelling). Cotton maturity and the relative thickness of the secondary wall, is widely evaluated by two ratio numbers, circularity (C) and degree of thickening ($T_r$), which can be derived from the above measurements using:

$$C=4\pi A/P_c^2,$$

$$T_r=2\pi T/P_c.$$

The theoretical ranges for both $T_r$ and C are [0,1].

The present invention is also used to analyze the cross-section of cotton fibers. Samples of 18 different cotton varieties were collected and cross-sectioned at SRRC and ITC. In one example, the present invention was used to examine 5-12 fields of images for each of the first collection of 11 varieties, and about 300 fields of images for each of the second collection of seven varieties. Table I presents the averages and the coefficients of variance CV (in the parentheses) of the cross-sectional data of the first 11 varieties. Due to the difference in the number of available images and the density of embedded fibers, the actual number of the analyzed fibers for each variety, N, varies from 206 to 851. Compared to the other measurements, the measurements on cotton perimeters $P_c$ show relatively low CVs across all the varieties. The reason is that the wall area ($A_c$), thickness (T) and lumens ($A_l$ and $P_l$) are influenced by the growing time of individual fibers, while the cotton perimeters ($P_c$) are basically invariant to the growing time. Cotton lumens can also change after the termination of growing. The lumens of dead fibers may totally disappear when the tubular fibers collapse. The lumens of some dead fibers may totally disappear when the fibers collapse. Therefore, only $P_c$ should be used to describe the fineness of the fiber. For the purpose of characterizing cotton fineness and maturity, the perimeter and area of lumens ($A_l$ and $P_l$) are not reliable parameters. Table III lists the cross-sectional measurements of cotton fibers.

concentrate more in the lower range of C-$T_r$. In fact, the C-$T_r$ plots of the rest variety samples all exhibit similar features.

Figure 26A:
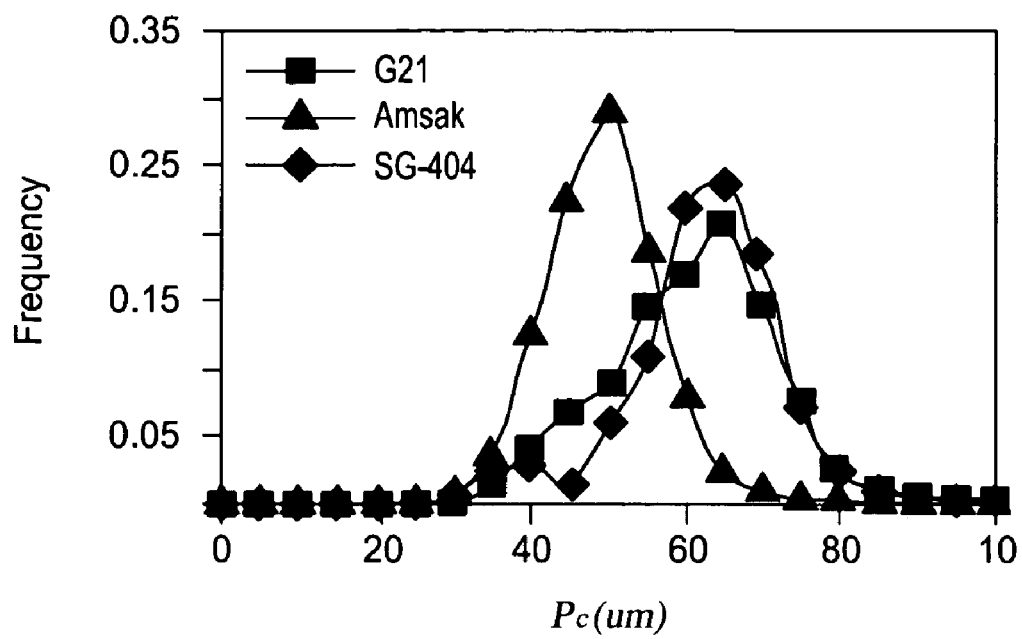
FIG. 26 is a plot of the distribution of fiber perimeters and the circularity.
Figure 26B:
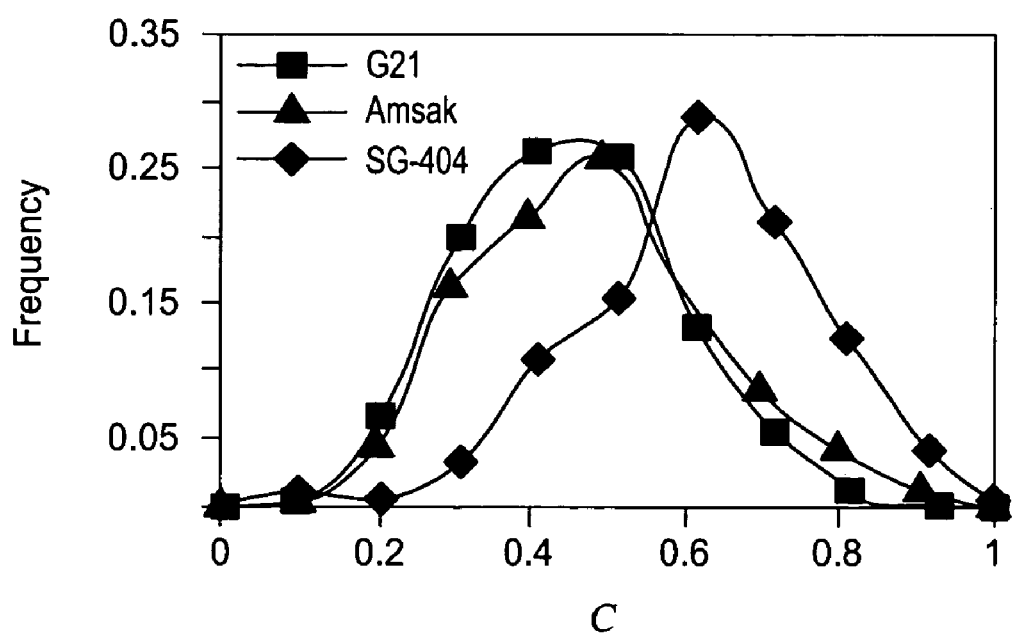

FIG. 26 displays the frequency distributions of fiber perimeters ($P_c$) and circularity (C) of three varieties varying in maturity, G21 (low), Amsak (medium) and SG-404 (high). Although G21 and SG404 have similar mean perimeters, the fineness of fibers in G21 is more widely distributed than those in SG-404. On the other hand, Amsak has a lower mean perimeter but a higher concentration in the perimeter distribution than G21 and SA-404. The differences in maturity among the three varieties are also reflected by the distinct distributions of their circularity data.

Figure 27:
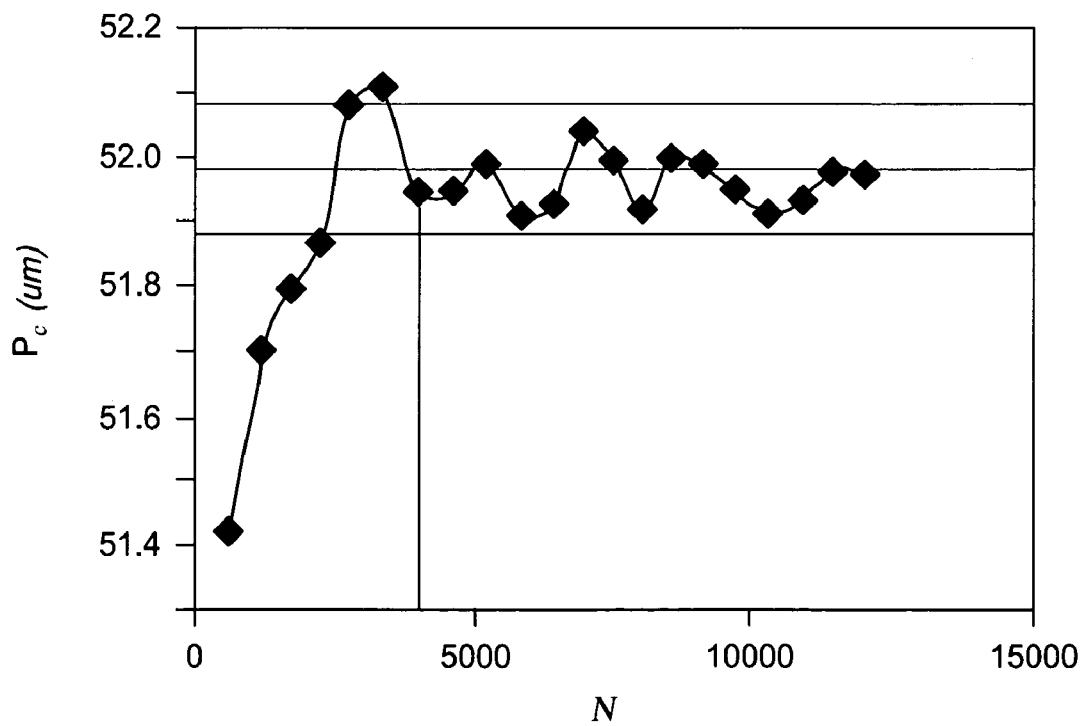
FIG. 27 is a plot of the variations of fiber perimeter with the number of analyzed fibers.

For cottons of the last seven varieties collected by ITC, 21 subsets of samples were taken for each variety and around 15 fields of images were grabbed for each subset. The number of the analyzed fibers of each variety reached more than 12,000, which is useful for examining variations of the measurements with the numbers of analyzable fibers. FIG. 27 shows the fluctuations of the average cotton perimeter ($P_c$) with the increase of the analyzed fibers (N) in a variety. $P_c$ may demonstrate variations when the number of the analyzed fibers is low, and fluctuates within small ranges (±0.2%) after more than 4000 measurements are taken into account for this variety.

The present invention also includes algorithms for implementing transverse scans along the longitudinal axis of a fiber. Each transverse scan yields a width measurement on a fiber ribbon. Cotton fibers are convoluted along their longitudinal axes, and a convoluted fiber has varying widths as projected in a 2-D image. Therefore, the scanned width changes with the position on a fiber. A high convolution often indicates a low level of maturity in a fiber [21, 29]. For a scanned fiber, the statistics of the width measurements are used to describe the fineness and maturity of the fiber. The

TABLE III

| Variety | N | $P_c$ (μm) | $A_c$ (μm²) | $P_l$ (μm) | $A_l$ (μm²) | T (μm) | $T_r$ | C |
|---|---|---|---|---|---|---|---|---|
| A21 | 405 | 56.96 (0.18) | 138.71 (0.30) | 34.28 (0.33) | 26.02 (0.42) | 3.44 (0.32) | 0.39 (0.36) | 0.55 (0.25) |
| C37 | 408 | 55.65 (0.15) | 116.06 (0.32) | 36.34 (0.26) | 23.07 (0.39) | 2.92 (0.35) | 0.34 (0.40) | 0.48 (0.32) |
| D6 | 480 | 46.18 (0.17) | 97.25 (0.33) | 25.29 (0.34) | 16.29 (0.43) | 3.02 (0.31) | 0.42 (0.34) | 0.58 (0.26) |
| G21 | 577 | 58.66 (0.21) | 103.82 (0.38) | 39.17 (0.31) | 23.45 (0.45) | 2.38 (0.31) | 0.27 (0.36) | 0.39 (0.33) |
| Amsak | 625 | 47.13 (0.18) | 74.56 (0.37) | 29.61 (0.33) | 16.30 (0.61) | 2.20 (0.37) | 0.30 (0.42) | 0.44 (0.36) |
| DPL-15 | 563 | 58.77 (0.18) | 110.55 (0.37) | 38.71 (0.30) | 23.26 (0.55) | 2.52 (0.39) | 0.28 (0.46) | 0.41 (0.37) |
| Giza-45 | 617 | 47.17 (0.20) | 94.74 (0.33) | 28.17 (0.35) | 17.06 (0.49 | 2.84 (0.31) | 0.40 (0.37) | 0.55 (0.27) |
| Gica-75 | 851 | 50.61 (0.23) | 111.09 (0.43) | 29.18 (0.40) | 17.34 (0.54) | 3.19 (0.40) | 0.41 (0.48) | 0.55 (0.43) |
| HS-26 | 206 | 59.42 (0.18) | 138.39 (0.41) | 35.76 (0.34) | 21.01 (0.50) | 3.25 (0.40) | 0.35 (0.41) | 0.49 (0.33) |
| Pima | 546 | 46.97 (0.19) | 87.79 (0.42) | 27.68 (0.37) | 16.81 (0.58) | 2.64 (0.43) | 0.36 (0.45) | 0.51 (0.34) |
| SG-404 | 518 | 60.37 (0.19) | 160.95 (0.37) | 34.42 (0.35) | 22.44 (0.46) | 3.80 (0.35) | 0.40 (0.36) | 0.56 (0.27) |

Figure 24:
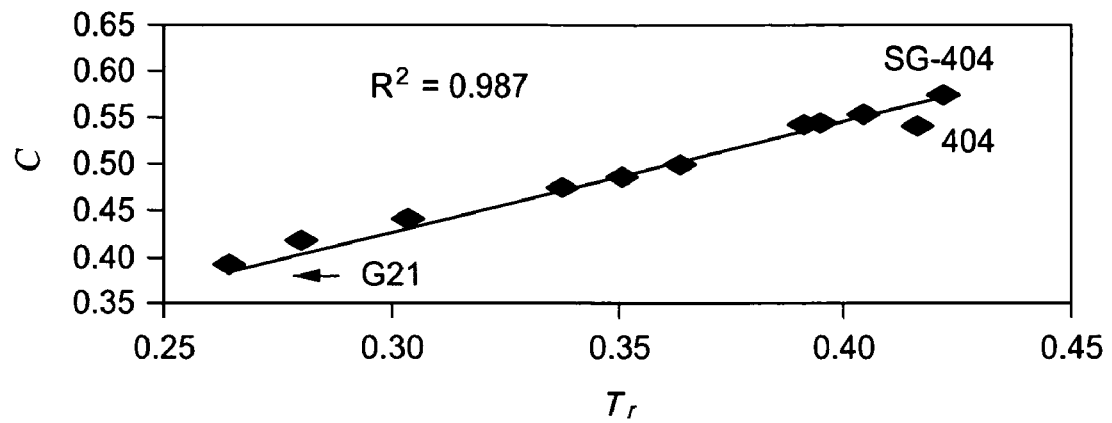
FIG. 24 is a plot of the correlation between circularity and the degree of thickening.
Figure 28A:
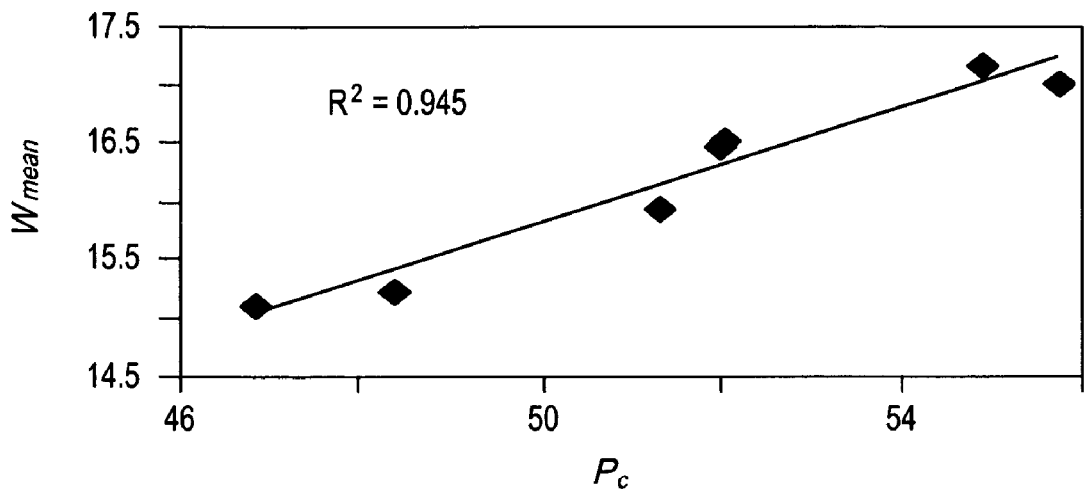
FIG. 28 is a plot of the correlation of the cross-sectional and the longitudinal data.
Figure 28B:
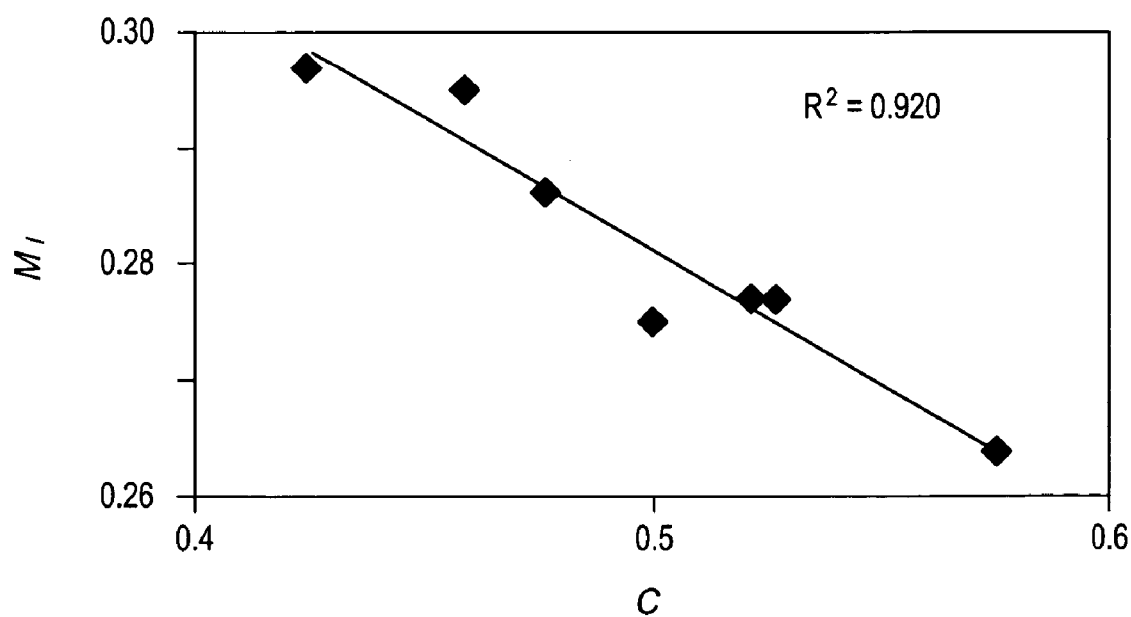
Figure 29A:
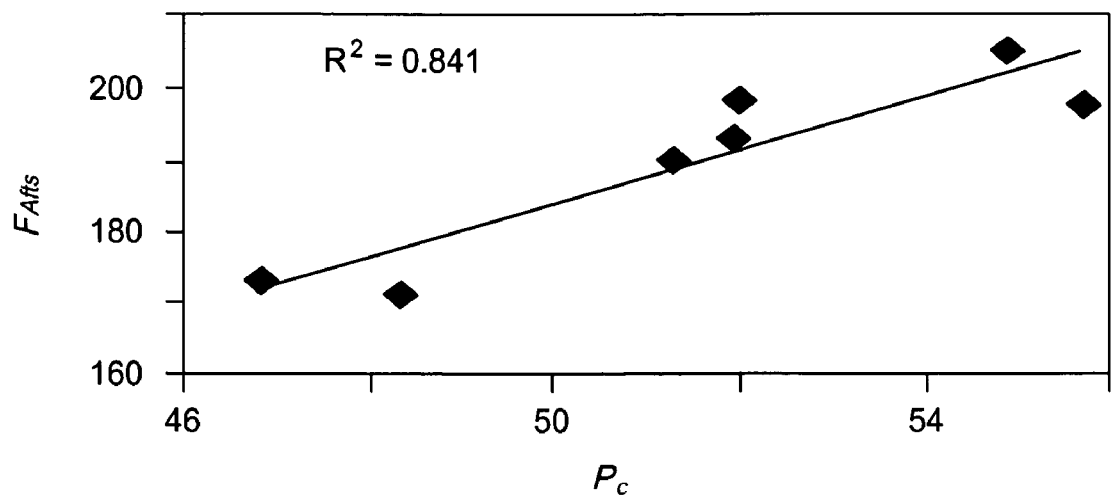
FIG. 29 is a plot of the correlation of the cross-sectional data and the AFIS data.
Figure 29B:
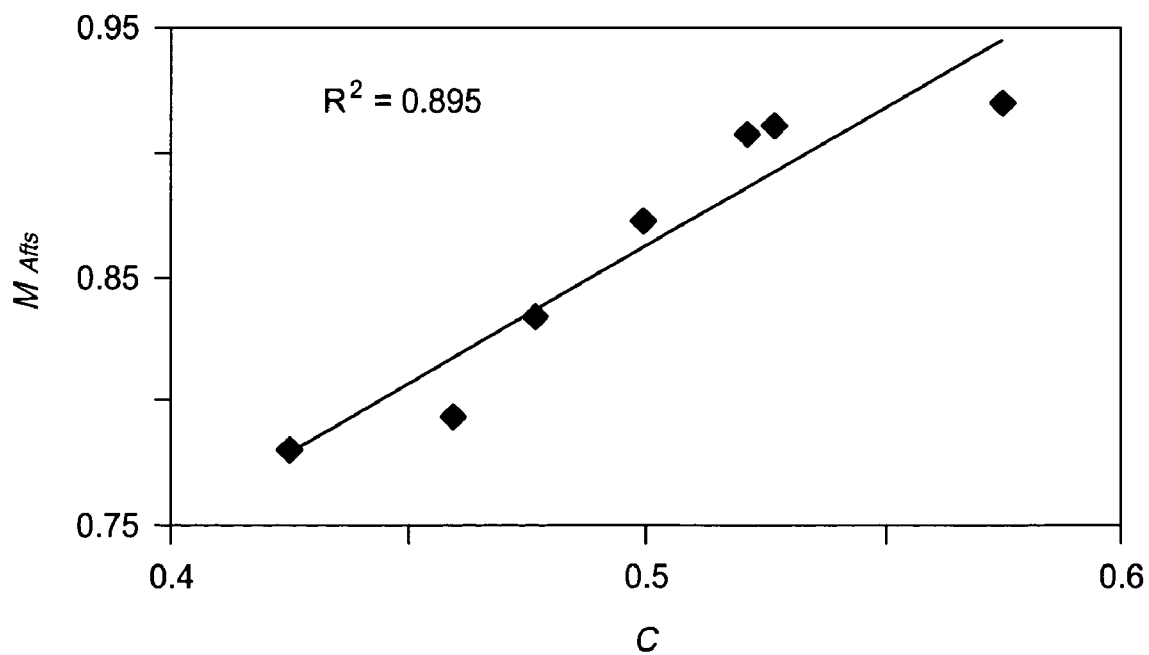

The degree of thickening ($T_r$) and the circularity (C) are the two independent measures of cotton maturity based on their definitions. FIG. 24 shows the data of these two parameters over the 11 varieties. $T_r$ and C are highly correlated, each of which can be used as a reliable measure of cotton maturity. However, the narrow ranges of C and $T_r$ in the figure are not sufficient for reflecting the C-$T_r$ relationship. The samples with the highest (SG-404) and the lowest (G21) maturity values in Table III were selected to show the C-$T_r$ relationship over a wider range. FIG. 25 displays the C-$T_r$ data of individual fibers in the G21 and SG-404 samples, in which the maturity of most fibers is visually different. The both plots reveal consistently high correlations and slight non-linearity between C and $T_r$ over the full range of [0, 1]. Because G21 has lower maturity than SG-404, the C-$T_r$ data points of G21 maturity based on the longitudinal measurements, $M_l$, can be defined as: $M_l=W_{sd}/W_{mean}$. Where $W_{mean}$ and $W_{sd}$ denote the mean and the standard deviation of the scanned widths. FIG. 28 displays the high correlations of fineness and maturity data of cross-sectional and longitudinal measurements of the last seven variety samples. FIG. 29 illustrates the correlation between the data of the present invention and data obtained from an Advanced Fiber Information System (AFIS), where $F_{Afis}$ and $M_{Afis}$ stand for the AFIS fineness and maturity, respectively. However, the circularity data in the cross-sectional measurements have a fairly low correlation with the micronaire data ($R^2=0.456$), e.g., a micronaire value is a combined measure of both fineness and maturity [30].

The present invention includes an algorithm for processing cotton cross-sectional images. The algorithms increase the automation and accuracy in separating touching fibers, identifying lumens, and taking measurements pertaining to cotton fineness and maturity. The correlation study illustrates that the two independent maturity measurements, degree of thickening and circularity, are highly correlated and possess a slightly non-linear relationship. The perimeter measurement presents the least variability among all the cross-sectional measurements, because the fiber perimeters of the same variety do not change with the growing time or maturity.

The present invention includes a method of monitoring the fineness and maturity of one or more fibers by acquiring one or more images of the one or more fibers and processing the images to identify characteristics of the one or more fibers. The processing includes determining the intensity of one or more regions of the one or more images, comparing the intensity of one of the one or more regions to the intensity of another of the one or more regions, and designating the fineness and maturity of the one or more fibers. The one or more images are cross-sectional images, transverse images or a combination thereof.

The processing step further includes removing one or more boundary pixels from the one or more images of the one or more fibers, wherein the one or more boundary pixels have three or fewer black neighboring pixels and re-scanning the one or more images for the one or more boundary pixels until no black pixel exists in the image. The method further includes identifying one or more holes that fall on the one or more fibers to produce a lumen image and omitting the one or more holes that do not pass through the one or more fibers. The one or more images of the one or more fibers and the lumen image are merged and the pixels in the one or more images of the one or more fibers and the pixels in the lumen image are compared, wherein identical pixels are set to black.

The processing provides records, which indicates fiber convolution, the fineness and maturity of the one or more fibers and includes the number of scans ($N_s$) the length of the scanned segments ($L_s$), the maximum ($W_{max}$), minimum ($W_{min}$), mean ($W_{mean}$) and standard deviation ($W_{sd}$) of fiber widths, and the number of twists ($N_t$) for each scanned fiber or combinations thereof. The records and data may then be outputted to a display, plotter, storage device, printer and combinations thereof to provide indications of fiber convolutions fineness and maturity.

For example, the present invention provides a system for determining the maturity of one or more fibers including a digital imaging device positioned to capture one or more images of one or more fibers and an image processing device that processes the one or more images to identify one or more fiber characteristics. The imaging processing device determines the intensity of one or more regions of the one or more images and compares the intensity of one of the one or more regions to the intensity of another of the one or more regions. The system also includes a display device in communication with the image processing device to display data the one or more fiber characteristics. The display device is a printer, plotter, monitor, storage device or a combination thereof.

The system also includes a motorized stage that automatically transports the fibers to allow the camera to grab fiber images at many different positions. The digital imaging device is a photodiode, charge coupled device, time delay integration device, array of charge coupled devices, time delay integration array of photosensitive elements or a combination thereof and has one or more sensors that detect, electromagnetic radiation, UV wavelength, IR wavelength, near IR wavelength, visible wavelength, laser, sound waves, magnetic fields, radar signals thermal variations and combinations thereof.

A fiber maturity measurement apparatus is provided for determining conditions of one or more fibers conditions having a digital imaging device positioned to capture one or more images of one or more fibers and an image processing device that processes the one or more images to identify fiber characteristics. The imaging processing device determines the intensity of one or more regions of the one or more images, compares the intensity of one of the one or more regions to the intensity of another of the one or more regions. The digital imaging device includes a photodiode, charge coupled device, time delay integration device, array of charge coupled devices, time delay integration array of photosensitive elements or a combination thereof.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Rubben, H., Lutzeyer, W., Fischer, N. et al.: Natural history and treatment of low and high risk superficial bladder tumors. J Urol, 139: 283, 1988.
2. Millan-Rodriguez, F., Chechile-Toniolo, G., Salvador-Bayarri, J. et al.: Primary superficial bladder cancer risk groups according to progression, mortality and recurrence. J Urol, 164: 680, 2000.
3. Heney, N. M.: Natural history of superficial bladder cancer. Prognostic features and long-term disease course. Urol Clin North Am, 19: 429, 1992.
4. Heney, N. M., Ahmed, S., Flanagan, M. J. et al.: Superficial bladder cancer: progression and recurrence. J Urol, 130: 1083, 1983.
5. Mizutani, Y., Yoshida, O., Bonavida, B.: Prognostic significance of soluble Fas in the serum of patients with bladder cancer. J Urol, 160: 571, 1998.
6. Nagata, S.: Fas and Fas ligand: a death factor and its receptor. Adv Immunol, 57: 129, 1994.
7. Kagi, D., Vignaux, F., Ledermann, B. et al.: Fas and perform pathways as major mechanisms of T cell-mediated cytotoxicity. Science, 265: 528, 1994.
8. Arase, H., Arase, N., Saito, T.: Fas-mediated cytotoxicity by freshly isolated natural killer cells. J Exp Med, 181: 1235, 1995.
9. Mizutani, Y., Hongo, F., Sato, N. et al.: Significance of serum soluble Fas ligand in patients with bladder carcinoma. Cancer, 92: 287, 2001.
10. Mizutani, Y., Yoshida, O., Ukimura, O. et al.: Prognostic significance of a combination of soluble Fas and soluble Fas ligand in the serum of patients with Ta bladder cancer. Cancer Biother Radiopharm, 17: 563, 2002.
11. Perabo, F. G., Mattes, R. H., Wirger, A. et al.: Soluble Fas and Fas-ligand in bladder cancer in vitro and in vivo. Urol Oncol, 6: 163, 2001.

12. DeLong, B. R., DeLong, D. M., Clarke-Pearson, D. L.: Comparing the areas under two or more correlated receiver operating characteristic curves: a nonparametric approach. Biometrics, 44: 837, 1988.
13. Pawelec, G.: Immunotherapy and immunoselection—tumour escape as the final hurdle. FEBS Lett, 567: 63, 2004.
14. O'Connell, J., Houston, A., Bennett, M. W. et al.: Immune privilege or inflammation? Insights into the Fas ligand enigma. Nat Med, 7: 271, 2001.
15. Lee, S. H., Lee, J. Y., Park, W. S. et al.: Transitional cell carcinoma expresses high levels of Fas ligand in vivo. BJU Int, 83: 698, 1999.
16. Chopin, D., Barei-Moniri, R., Maille, P. et al.: Human urinary bladder transitional cell carcinomas acquire the functional Fas ligand during tumor progression. Am J Pathol, 162: 1139, 2003.
17. Liu, C., Cheng, J., Mountz, J. D.: Differential expression of human Fas mRNA species upon peripheral blood mononuclear cell activation. Biochem J, 310 (Pt 3): 957, 1995.
18. Lotan, Y., Roehrborn, C. G.: Sensitivity and specificity of commonly available bladder tumor markers versus cytology: results of a comprehensive literature review and meta-analyses. Urology, 61: 109, 2003.
19. Glas, A. S., Roos, D., Deutekom, M. et al.: Tumor markers in the diagnosis of primary bladder cancer. A systematic review. J Urol, 169: 1975, 2003.
20. Mizutani, Y., Yoshida, O., Bonavida, B.: Prognostic significance of soluble Fas in the serum of patients with bladder cancer. J Urol, 160: 571, 1998.
21. Nagata, S.: Fas and Fas ligand: a death factor and its receptor. Adv Immunol, 57: 129, 1994.
22. Kagi, D., Vignaux, F., Ledermann, B., Burki, K., Depraetere, V., Nagata, S. et al.: Fas and perform pathways as major mechanisms of T cell-mediated cytotoxicity. Science, 265: 528, 1994.
23. Arase, H., Arase, N., Saito, T.: Fas-mediated cytotoxicity by freshly isolated natural killer cells. J Exp Med, 181: 1235, 1995.
24. Mizutani, Y., Hongo, F., Sato, N., Ogawa, O., Yoshida, O., Miki, T.: Significance of serum soluble Fas ligand in patients with bladder carcinoma. Cancer, 92: 287, 2001.
25. Mizutani, Y., Yoshida, O., Ukimura, O., Kawauchi, A., Bonavida, B., Miki, T.: Prognostic significance of a combination of soluble Fas and soluble Fas ligand in the serum of patients with Ta bladder cancer. Cancer Biother Radiopharm, 17: 563, 2002.
26. Perabo, F. G., Mattes, R. H., Wirger, A., Steiner, G., Kamp, S., Schmidt, D. et al.: Soluble Fas and Fas-ligand in bladder cancer in vitro and in vivo. Urol Oncol, 6: 163, 2001.
27. DeLong, B. R., DeLong, D. M., Clarke-Pearson, D. L.: Comparing the areas under two or more correlated receiver operating characteristic curves: a nonparametric approach. Biometrics, 44: 837, 1988.
28. Pawelec, G.: Immunotherapy and immunoselection—tumour escape as the final hurdle. FEBS Lett, 567: 63, 2004.
29. O'Connell, J., Houston, A., Bennett, M. W., O'Sullivan, G. C., Shanahan, F.: Immune privilege or inflammation? Insights into the Fas ligand enigma. Nat Med, 7: 271, 2001.
30. Lee, S. H., Lee, J. Y., Park, W. S., Kim, S. Y., Jang, J. J., Yoo, N. J.: Transitional cell carcinoma expresses high levels of Fas ligand in vivo. BJU Int, 83: 698, 1999.
31. Chopin, D., Barei-Moniri, R., Maille, P., Le Frere-Belda, M. A., Muscatelli-Groux, B., Merendino, N. et al.: Human urinary bladder transitional cell carcinomas acquire the functional Fas ligand during tumor progression. Am J Pathol, 162: 1139, 2003.
32. Liu, C., Cheng, J., Mountz, J. D.: Differential expression of human Fas mRNA species upon peripheral blood mononuclear cell activation. Biochem J, 310 (Pt 3): 957, 1995.
33. Lotan, Y., Roehrborn, C. G.: Sensitivity and specificity of commonly available bladder tumor markers versus cytology: results of a comprehensive literature review and meta-analyses. Urology, 61: 109, 2003.
34. Glas, A. S., Roos, D., Deutekom, M., Zwinderman, A. H., Bossuyt, P. M., Kurth, K. H.: Tumor markers in the diagnosis of primary bladder cancer. A systematic review. J Urol, 169: 1975, 2003.

What is claimed is:

1. A precision mechanical fiber cutting apparatus comprising:
a vertical blade moving mechanism that moves in a vertical plane;
at least 3 substantially vertical parallel fixed cutting blades connected to the vertical blade moving mechanism to move in a vertical plane to punch out one or more cut fibers;
a cutting stage positioned below the vertical blade moving mechanism to support a fiber sample against a downward cutting motion of the at least 3 substantially vertical parallel fixed cutting blades, wherein the cutting stage comprises
a top and a bottom connected to 1 or more side walls having an inlet aperture and an outlet aperture, wherein the top comprises at least 3 slits to receive the at least 3 substantially vertical parallel fixed cutting blades to allow transport of the fiber sample into the cutting stage, wherein the top supports the fiber sample to allow the at least 3 substantially vertical parallel fixed cutting blades to punch out the fiber sample into one or more cut fibers having substantially uniformed lengths with substantially uniformed ends;
a fiber chamber connected to the outlet aperture by a conduit to receive the one or more cut fibers; and
a pressurized gas source connected to the inlet aperture to transfer the one or more cut fibers to the fiber chamber, wherein the one or more cut fibers are deposited in a random distribution onto a sample slide within the fiber chamber.

2. The apparatus of claim 1, wherein the blade moving mechanism is a pneumatic ram, a hydraulic ram, an electric motor and combinations thereof.

3. The apparatus of claim 1, wherein the at least 3 substantially vertical parallel fixed cutting blades comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more fixed blades.

4. The apparatus of claim 1, wherein the at least 3 substantially vertical parallel fixed cutting blades individually comprise a conventional razor blade, a blade, a serrated blade, a metal wire, a plastic fiber, a composite fiber, a plastic blade, or a composite material.

5. The apparatus of claim 1, wherein the conduit comprises an inlet pressure fitting to allow an increase in pressure and an outlet aperture to allow a reduction in the pressure.

6. The apparatus of claim 1, wherein the pressurized gas source is a compressor, a tank, a gas line, or a combination thereof.

* * * * *

UNITED STATES PATENT AND TRADEMARK OFFICE
CERTIFICATE OF CORRECTION

PATENT NO.        : 7,588,438 B2
APPLICATION NO.   : 11/590067
DATED             : September 15, 2009
INVENTOR(S)       : Bugao Xu et al.

Page 1 of 1

It is certified that error appears in the above-identified patent and that said Letters Patent is hereby corrected as shown below:

In the Drawings
Sheet 6 of 23, FIG. 7A and FIG. 7B
Replace X axis title "Graysecale" with --Grayscale--

Col. 2, line 36
Replace "to increased accuracy" with --to increase accuracy--

Col. 3, line 57
Replace "do not passed through" with --do not pass through--

Col. 7, line 18
Replace "cutter blades create one" with --cutter blades creates one--

Col. 11, line 6
Replace "30 included a door" with --30 includes a door--

Col. 13, line 30
Replace "the adjusent neighbors" with --the adjacent neighbors--

Col. 16, line 48
Replace "can not be started" with --cannot be started--

Signed and Sealed this

Twenty-ninth Day of December, 2009

David J. Kappos
*Director of the United States Patent and Trademark Office*